US012668572B2

(12) United States Patent
Wang

(10) Patent No.: US 12,668,572 B2
(45) Date of Patent: Jun. 30, 2026

(54) DEGRADABLE LIPID FOR ACTIVE MOLECULE DELIVERY AND LIPID NANOPARTICLE THEREOF

(71) Applicant: BEIJING CARRIUS BIO LTD., Beijing (CN)

(72) Inventor: Ming Wang, Beijing (CN)

(73) Assignee: Beijing Carrius Bio Ltd., Beijing (CN)

( * ) Notice: Subject to any disclaimer, the term of this patent is extended or adjusted under 35 U.S.C. 154(b) by 0 days.

(21) Appl. No.: 18/961,247

(22) Filed: Nov. 26, 2024

(65) Prior Publication Data

US 2025/0179015 A1 Jun. 5, 2025

Related U.S. Application Data

(63) Continuation of application No. PCT/CN2024/119091, filed on Sep. 14, 2024.

(30) Foreign Application Priority Data

Sep. 27, 2023 (CN) ........................ 202311261516.7

(51) Int. Cl.
*C07C 323/12* (2006.01)
*A61K 9/51* (2006.01)
*A61K 48/00* (2006.01)

(52) U.S. Cl.
CPC .......... *C07C 323/12* (2013.01); *A61K 9/5123* (2013.01); *A61K 48/0033* (2013.01)

(58) Field of Classification Search
None
See application file for complete search history.

(56) References Cited

U.S. PATENT DOCUMENTS

2014/0308304 A1 10/2014 Manoharan et al.

FOREIGN PATENT DOCUMENTS

| | | | |
|---|---|---|---|
| CN | 110101665 | * | 8/2019 |
| CN | 117865863 | A | 4/2024 |
| WO | 2013086373 | A1 | 6/2013 |
| WO | 2023165595 | A1 | 9/2023 |

OTHER PUBLICATIONS

Chan et al., "Computational and Experimental Approaches to Investigate Lipid Nanoparticles as drug and Gene Delivery Systems," Curr. Top Med. Chem., 21(2):92-114, 2021.
Liu et al., "Membrane-destabilizing ionizable phospholipids for organ-selective mRNA delivery and CRISPR-Cas gene editing," Nat. Mater., 20:701-710, 2021.
Qiu et al., "Lung-selective mRNA delivery of synthetic lipid nanoparticles for the treatment of pulmonary lymphangioleiomyomatosis," PNAS, 119(8):1-10, 2022.
Chang et al., "Enzyme-Instructed Activation of Pro-protein Therapeutics (PPT) In Vivo", Journal of the American Chemical Society, Oct. 7, 2019, vol. 141, Issue 45, 16 pages.
International Search Report and Written Opinion, PCT/C2024/119091, International Searching Authority, China National Intellectual Property Administration, Dec. 4, 2024.
Liang et al., "Selective RNA Interference and Gene Silencing Using Reactive Oxygen Species-responsive Lipid Nanoparticles", Chemical Communications, Jun. 13, 2019, 55, pp. 8170-8173.
Office Action and Search Report, Application No. 202311261516.7, China National Intellectual Property Administration, Jun. 5, 2024.

* cited by examiner

*Primary Examiner* — Ana Z Muresan
(74) *Attorney, Agent, or Firm* — Travis Young; Bozicevic, Field & Francis LLP

(57) ABSTRACT

The present invention provides an ionizable lipid compound having an optimized carbon chain length and an amine head so that the ionizable lipid compound has increased delivery efficiency for an active molecule including, but not limited to, nucleic acids, proteins, small molecule drugs and the like. The present invention further relates to a lipid nanoparticle (LNP) comprising the ionizable lipid compound and the active molecule, and a pharmaceutical composition comprising the lipid nanoparticle.

19 Claims, 5 Drawing Sheets

DEGRADABLE LIPID FOR ACTIVE MOLECULE DELIVERY AND LIPID NANOPARTICLE THEREOF

CROSS REFERENCE TO RELATED APPLICATIONS

This application is a continuation of PCT/CN2024/119091, filed Sep. 14, 2024, which application claims priority to Chinese Patent Application No. 202311261516.7, filed Sep. 27, 2023. The disclosure of which are incorporated herein by reference in their entirety for all purposes.

TECHNICAL FIELD

The present invention provides an ionizable lipid compound having an optimized carbon chain length and an ionizable amine head structure so as to achieve efficient delivery of an active molecule including, but not limited to, nucleic acids, proteins, small molecule drugs and the like. The present invention further relates to a lipid nanoparticle (LNP) comprising the ionizable lipid compound and the active molecule, and a pharmaceutical composition comprising the lipid nanoparticle.

BACKGROUND ART

Biomacromolecules such as nucleic acids and proteins have great advantages and potential in the regulation of gene expression and the prevention and treatment of malignant diseases; however, biomacromolecules are a class of charged molecules with strong hydrophilicity, which are difficult to penetrate the cell membrane into the cell, and in addition, nucleic acid drugs such as RNAs are easily degraded by nucleases, which limits their stability in vivo and further limits the druggability of RNAs.

A lipid nanoparticle (LNP) is generally composed of four components: a cationic or ionizable lipid, a phospholipid, cholesterol and a PEG lipid. The LNP can encapsulate nucleic acid drug molecules such as RNAs and protect them from nuclease degradation, and has a high degree of stability and biocompatibility, and thus it has become a promising drug delivery system and has been clinically applied.

The drug delivery efficiency of the LNP is affected by its composition. In the LNP, the amine head part (amine head) of the cationic lipid or ionizable lipid can promote the binding and encapsulation of the LNP and a biomacromolecule, through electrostatic interaction with the biomacromolecule, and improve the efficiency of LNP uptake by cells. Studies have shown that the hydrophobic carbon chain length of cationic lipids or ionizable lipids affects stability of LNPs and the efficiency of drug encapsulation and delivery. For example, Min Qiu et al. (*PNAS* 2022, 119, e2116271119) reported that the delivery efficiency of LNPs increases with the increase of the length of lipid hydrophobic carbon chain, and for example, a lipid molecule with a hydrophobic chain of 16 carbon atoms show the highest nucleic acid delivery efficiency as compared with lipid molecules with hydrophobic chains of 12-14 carbon atoms; Chun Chan et al. (*Curr Top Med Chem* 2021, 21, 92-114) also reported that lipid molecules with a carbon chain length of 12 to 18 carbon atoms provide sufficient fluidity and rigidity for LNPs; and Shuai Liu et al. (*Nature Mater,* 2021, 20, 701-710) showed in FIG. 2*e* of this document that the carbon chain length affects the delivery efficiency of nucleic acid drugs, and lipid molecules with a carbon chain length of 10, 11 and 12 carbon atoms have higher delivery efficiency.

In summary, the hydrophobic carbon chain length of cationic lipids or ionizable lipids affects the formation of LNPs and the drug delivery efficiency. Therefore, a balance of these factors needs to be considered when designing LNPs to improve their delivery efficiency and stability in vivo.

SUMMARY OF THE INVENTION

The present invention provides an ionizable lipid compound with an optimized hydrophobic carbon chain length and an amine head. The inventors of the present invention have found that unlike cationic lipids or ionizable lipid compounds having a carbon chain length of 12 to 18 carbon atoms in the prior art, further decreasing the hydrophobic carbon chain length instead leads to increased delivery efficiency for the ionizable lipid compound of this structure of the present invention. For this reason, the present invention is completed by the inventors of the present invention.

In a first aspect, the present invention provides a lipid compound of formula (I), (I)

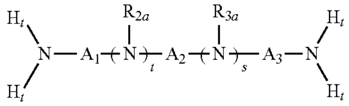

wherein $R_{2a}$ and $R_{3a}$ are each independently hydrogen, a monovalent aliphatic group, a monovalent heteroaliphatic group, a monovalent aromatic group, a monovalent heteroaromatic group, or Ht;

t and s are each independently 0 or 1, and when t or s is zero, it means that the part is directly a single bond, provided that t and s are not both 0;

$A_1$, $A_2$, and $A_3$ are each independently a single bond, a divalent aliphatic group, a divalent heteroaliphatic group, a divalent aromatic group, or a divalent heteroaromatic group, or a combination of two of the above;

each Ht is independently at each occurrence —$R_1$—X—$R_2$—Y—$R_3$—Z—$R_4$, wherein each $R_1$ is independently at each occurrence a divalent aliphatic group, a divalent heteroaliphatic group, a divalent aromatic group, or a divalent heteroaromatic group;

each X is independently at each occurrence

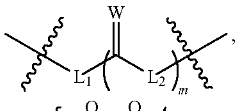
,
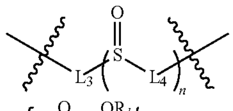
,
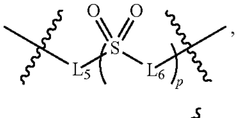
,
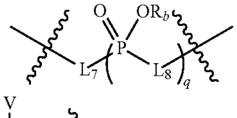
, or
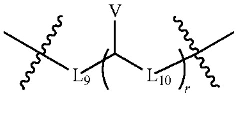
, wherein m, n, p, q, and r are each independently 1-6;

W is O, S, or $NR_c$;

$L_1$, $L_3$, $L_5$, $L_7$, and $L_9$ are directly connected to $R_1$ or $R_2$ and are each independently a single bond, O, S, or $NR_d$;

$L_2$, $L_4$, $L_6$, $L_8$, and $L_{10}$ are each independently a bond, O, S, or $NR_c$;

V is an aliphatic group, $OR_f$, $SR_g$, or $NR_hR_i$, wherein $R_b$, $R_c$, $R_d$, $R_e$, $R_f$, $R_g$, $R_h$, and $R_i$ are each independently hydrogen, hydroxyl, an oxyaliphatic group, a monovalent aliphatic group, a monovalent heteroaliphatic group, a monovalent aromatic group, or a monovalent heteroaromatic group;

Y and Z are each independently at each occurrence S or O;

each $R_2$ is independently at each occurrence a single bond, a divalent aliphatic group, a divalent heteroaliphatic group, a divalent aromatic group, or a divalent heteroaromatic group;

each $R_3$ is independently at each occurrence a single bond, a divalent aliphatic group, a divalent heteroaliphatic group, a divalent aromatic group, or a divalent heteroaromatic group;

each $R_4$ is independently at each occurrence a hydrophobic group selected from $-(CH_2CH_2O)_y-C_3\text{-}C_8$ alkyl, $-(CH_2CH_2O)_y-C_3\text{-}C_8$ alkenyl or $-(CH_2CH_2O)_y-C_3\text{-}C_8$ alkynyl, wherein y is 0 or 1 or 2.

In some embodiments, t and s are both 0; or t is 0 and s is 1; or t is 1 and s is 0.

In some embodiments, $R_1$ is a $C_{1-6}$ (e.g., $C_{1-4}$) divalent aliphatic group or a $C_{1-6}$ (e.g., $C_{1-4}$) divalent heteroaliphatic group, preferably a $C_{1-4}$ divalent alkyl or a $C_{1-4}$ divalent heteroalkyl.

In some embodiments, X is

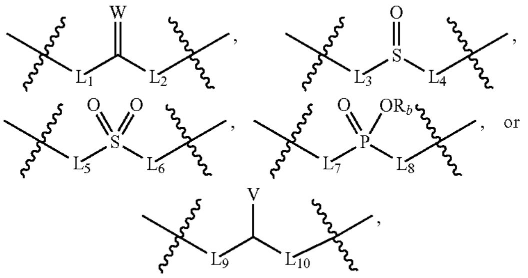

, , , or , wherein each variable is as defined for formula (I). In a further embodiment, $L_1$, $L_3$, $L_5$, $L_7$, and $L_9$ are connected to $R_1$ and are each independently a single bond, O, S, or NH. In a further embodiment, X is

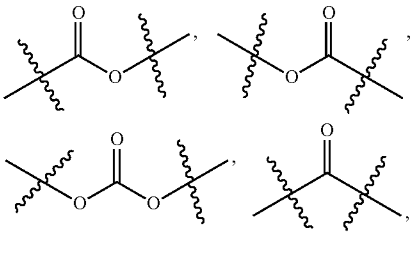

, , , ,

-continued

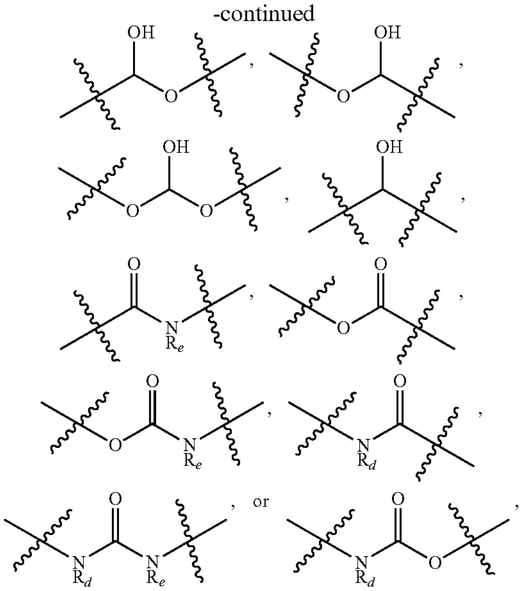

, , , , , , , , or , wherein $R_d$ and $R_e$ are as defined for formula (I). In some embodiments, $R^d$ and $R^e$ are each independently H or a $C_{1-4}$ monovalent aliphatic group, preferably H or $C_{1-4}$ monovalent alkyl.

In some embodiments, Y and Z are both S; or Y is S and Z is O; or Y is O and Z is S; or Y and Z are both O.

In some embodiments, each $R_2$ is independently at each occurrence a single bond or a $C_{1-6}$ divalent aliphatic group (e.g., a $C_{1-4}$ divalent aliphatic group, preferably a $C_{1-4}$ divalent alkyl, more preferably a $C_{1-2}$ divalent alkyl).

In some embodiments, each $R_3$ is independently at each occurrence a single bond or a $C_{1-6}$ divalent aliphatic group (e.g., a $C_{1-4}$ divalent aliphatic group, preferably a $C_{1-4}$ divalent alkyl). In a further embodiment, each $R_3$ is independently at each occurrence a single bond, or

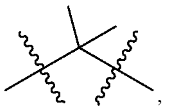 [SMILES: *C(*)(C)C]

, or methylene (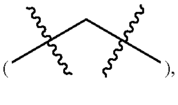), preferably

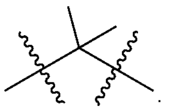 [SMILES: *C(*)(C)C]

.

In some embodiments, each $R_4$ is independently at each occurrence $C_3\text{-}C_8$ alkyl, $C_3\text{-}C_8$ alkenyl, $C_3\text{-}C_8$ alkynyl, $-(CH_2CH_2O)-C_3\text{-}C_8$ alkyl, $-(CH_2CH_2O)-C_3\text{-}C_8$ alkenyl, $-(CH_2CH_2O)-C_3\text{-}C_8$ alkynyl, $-(CH_2CH_2O)_2-C_3\text{-}$ $C_8$ alkyl, —$(CH_2CH_2O)_2$—$C_3$-$C_8$ alkenyl or —$(CH_2CH_2O)_2$ —$C_3$-$C_8$ alkynyl. In some embodiments, each $R_4$ is independently at each occurrence $C_4$-$C_8$ alkyl, $C_4$-$C_8$ alkenyl, $C_4$-$C_8$ alkynyl, —$(CH_2CH_2O)$—$C_4$-$C_8$ alkyl, —$(CH_2CH_2O)$—$C_4$-$C_8$ alkenyl, —$(CH_2CH_2O)_2$—$C_4$-$C_8$ alkynyl, —$(CH_2CH_2O)_2$—$C_4$-$C_8$ alkyl, —$(CH_2CH_2O)_2$—$C_4$-$C_8$ alkenyl or —$(CH_2CH_2O)_2$—$C_4$-$C_8$ alkynyl. In some embodiments, the alkyl in the $C_4$-$C_8$ alkyl, —$(CH_2CH_2O)$—$C_4$-$C_8$ alkyl or —$(CH_2CH_2O)_2$—$C_4$-$C_8$ alkyl is a linear alkyl; the alkenyl in the $C_4$-$C_8$ alkenyl, —$(CH_2CH_2O)$—$C_4$-$C_8$ alkenyl or —$(CH_2CH_2O)_2$—$C_4$-$C_8$ alkenyl is a linear alkenyl; and the alkynyl in the $C_4$-$C_8$ alkynyl, —$(CH_2CH_2O)$—$C_4$-$C_8$ alkynyl or —$(CH_2CH_2O)_2$—$C_4$-$C_8$ alkynyl is a linear alkynyl. In some embodiments, each $R_4$ is independently at each occurrence —$(CH_2CH_2O)$—$(CH_2)_3$ $CH_3$, —$(CH_2CH_2O)_2$—$(CH_2)_3CH_3$, —$(CH_2CH_2O)$—$(CH_2)_4CH_3$, —$(CH_2CH_2O)_2$—$(CH_2)_4$ $CH_3$, —$(CH_2CH_2O)$—$(CH_2)_5CH_3$, —$(CH_2CH_2O)_2$—$(CH_2)_5CH_3$, —$(CH_2CH_2O)$—$(CH_2)_6CH_3$, —$(CH_2CH_2O)_2$ —$(CH_2)_6CH_3$, —$(CH_2CH_2O)$—$(CH_2)_7CH_3$ or —$(CH_2CH_2O)_2$—$(CH_2)_7CH_3$.

In some embodiments, each Ht is independently at each occurrence

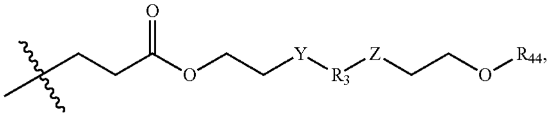

wherein Y and Z are both S; or Y is S and Z is O; or Y is O and Z is S; or Y and Z are both O; each $R_3$ is independently at each occurrence a single bond, or

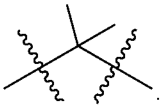

or methylene (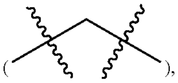), and $R_{44}$ is $C_4$-$C_8$ alkyl, $C_4$-$C_8$ alkenyl or $C_4$-$C_8$ alkynyl; and in some embodiments, each $R_4$ is independently at each occurrence —$(CH_2)_3CH_3$, —$(CH_2CH_2O)$—$(CH_2)_3CH_3$, —$(CH_2CH_2O)$—$(CH_2)_4CH_3$, —$(CH_2CH_2O)$—$(CH_2)_5CH_3$, —$(CH_2CH_2O)$—$(CH_2)_6CH_3$ or —$(CH_2CH_2O)$—$(CH_2)_7$ $CH_3$.

In the present invention, $A_1$, $A_2$ and $A_3$ form an amine head of the lipid, which undergoes an addition reaction with a hydrophobic lipid tail to obtain a series of lipids. Since the amine head can be protonated, such lipid nanoparticles are positively charged as a whole, so they can undergo an electrostatic interaction with negatively charged mRNAs, cell membranes and lysosomal membranes, such that such lipids can effectively encapsulate and deliver mRNAs. In some embodiments, the pKa value of the amine head is greater than 4, preferably greater than 6, and more preferably greater than 8.

In some embodiments, t is 1, s is 0, $A_2$ is a single bond, and $A_1$ and $A_3$ are each independently a divalent aliphatic group or a divalent heteroaliphatic group; in a further embodiment, $A_1$ and $A_3$ are each independently a $C_1$-$C_6$ divalent aliphatic group (e.g., a $C_1$-$C_4$ divalent aliphatic group, preferably $C_1$-$C_4$ divalent alkyl); and in a further embodiment, $A_1$ and $A_3$ are each independently —$CH_2CH_2$— or —$CH_2CH_2CH_2$—, and $R_{2a}$ is hydrogen or a monovalent aliphatic group, or is hydrogen or $C_1$-$C_6$ alkyl or methyl. In some embodiments, t is 1, s is 1, $A_1$, $A_2$ and $A_3$ are each independently a divalent aliphatic group or a divalent heteroaliphatic group; in a further embodiment, $A_1$, $A_2$ and $A_3$ are each independently a $C_1$-$C_6$ divalent aliphatic group (e.g., a $C_1$-$C_4$ divalent aliphatic group, preferably $C_1$-$C_4$ divalent alkyl); and in a further embodiment, $A_1$, $A_2$ and $A_3$ are each independently —$CH_2CH_2$— or —$CH_2CH_2CH_2$—, and $R_{2a}$ and $R_{3a}$ are each independently hydrogen or a monovalent aliphatic group, or is hydrogen or $C_1$-$C_6$ alkyl or methyl.

In some embodiments,

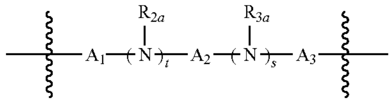

is

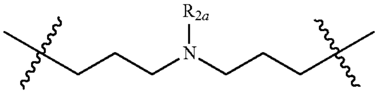

,

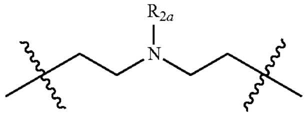

or

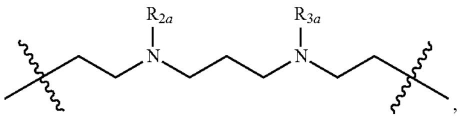

, wherein $R_{2a}$ and $R_{3a}$ are each independently hydrogen or a monovalent aliphatic group, or hydrogen or $C_1$-$C_6$ alkyl or methyl.

In some embodiments, the lipid of formula (I) is

YX8

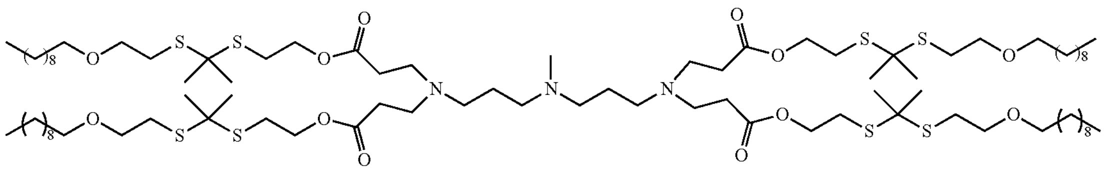

-continued

YX17

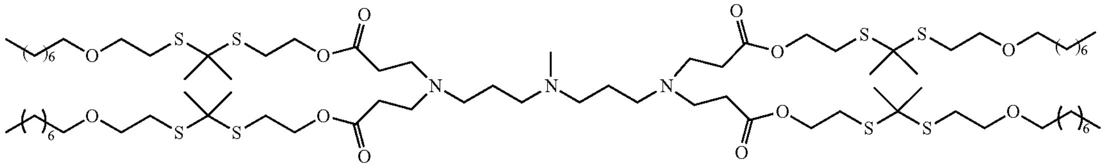

YX31

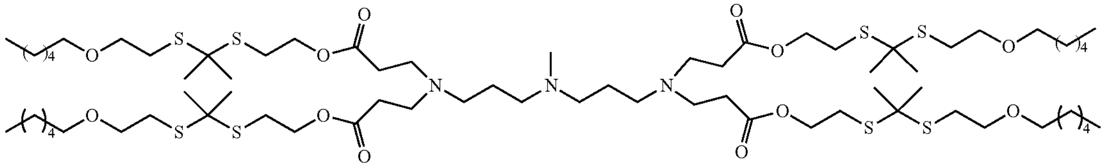

YX27

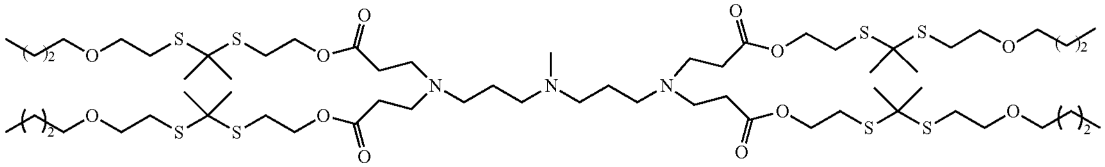

YX28

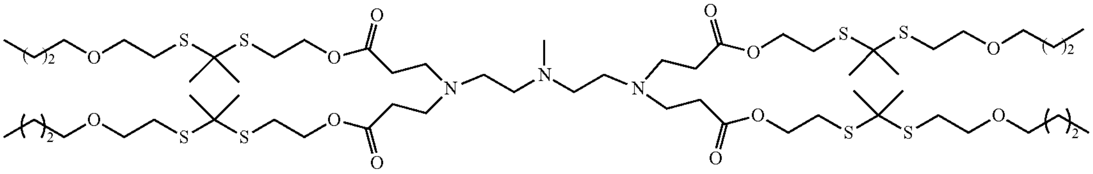

YX35

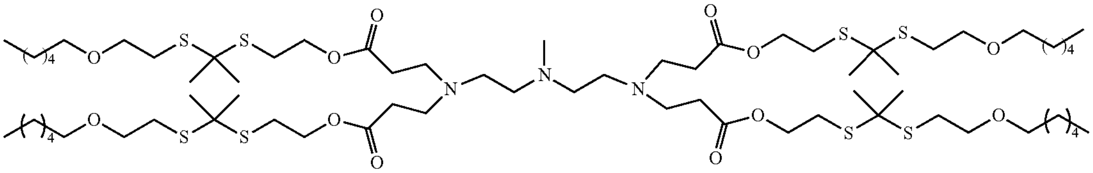

YX29

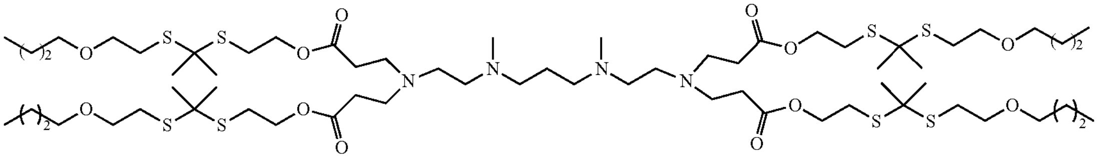

YX33

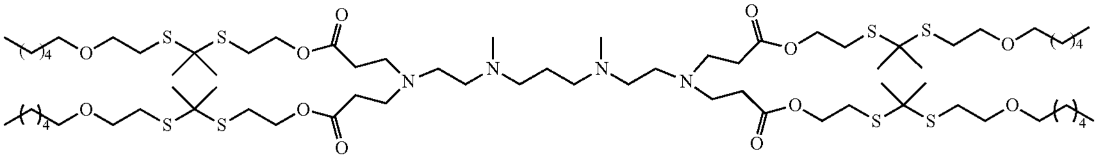

The lipid of formula (I) of the present invention is biodegradable due to the fact that the Ht group contains a corresponding ketal unit (especially a corresponding thioketal unit when Y and Z are both S). Such a lipid can efficiently bind an mRNA and assemble to form a nanostructure, and after entering a diseased cell, the lipid selectively responds to a highly oxidative environment in the cell and degrades, thus resulting in efficient release of the mRNA and expression of a corresponding protein.

In a second aspect, the present invention provides a method for preparing a lipid of formula (I) in which $R_1$ is ethylene, the method comprising:

mixing and reacting an acrylic compound of formula (II), i.e. $CH_2{=}CH{-}X{-}R_2{-}Y{-}R_3{-}Z{-}R_4$ (II), in which each variable is as defined for formula (I), with a hydrophilic amine at a molar ratio, wherein the molar ratio of the hydrophilic amine to the acrylate compound of formula (II) is greater than 4, for example 4.3:1 or 4.5:1, to ensure that the reaction is fully completed; and then optionally, purifying the product by column chromatography to obtain the desired lipid of formula (I);

wherein the variables $R_2$, X, Y, $R_3$, Z, and $R_4$ are as defined for formula (I). In some embodiments, X is

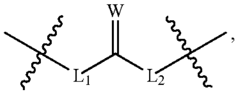 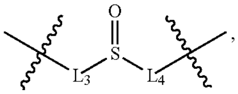

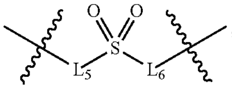 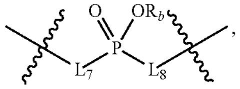 or

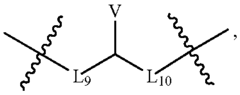

wherein each variable is as defined for formula (I). In a further embodiment, $L_1$, $L_3$, $L_5$, $L_7$, and $L_9$ are connected to $R_1$ and are each independently a single bond, O, S, or NH. In a further embodiment, X is 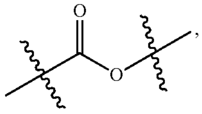 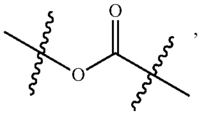

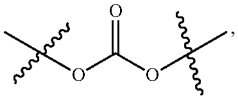 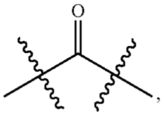

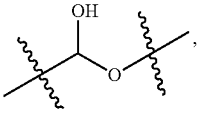 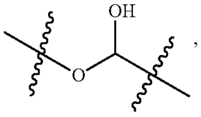

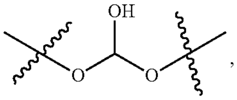 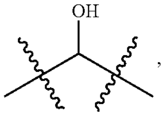

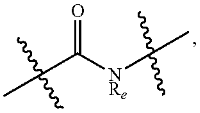 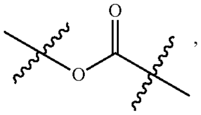

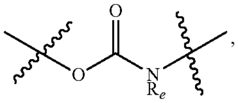 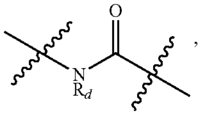

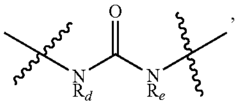 or 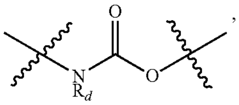

wherein $R_d$ and $R_e$ are as defined for formula (I). In some embodiments, $R^d$ and $R^e$ are each independently H or a $C_{1-4}$ monovalent aliphatic group, preferably H or $C_{1-4}$ monovalent alkyl.

In some embodiments, in method (a), the product is purified by column chromatography to obtain the desired lipid of formula (I), wherein the column chromatographic purification method is well known in the art.

In some embodiments, in the present invention, $A_1$, $A_2$ and $A_3$, together with the N to which they are attached, form an amine head of the lipid, which undergoes an addition reaction with a hydrophobic lipid tail to obtain a series of lipids. Since the amine head can be protonated, such lipid nanoparticles are positively charged as a whole, so they can undergo an electrostatic interaction with negatively charged mRNAs, cell membranes and lysosomal membranes, such that such lipids can effectively encapsulate and deliver mRNAs.

In some embodiments the hydrophilic amine in the method is selected from

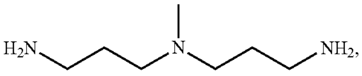

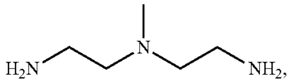

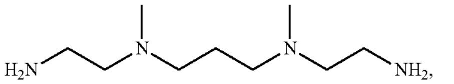

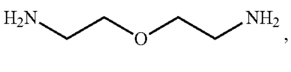 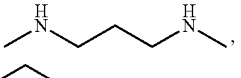

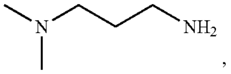 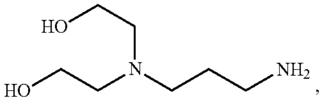

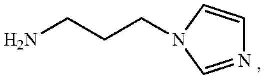 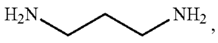

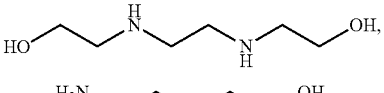

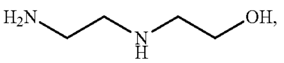

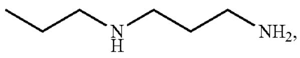

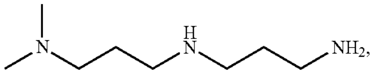

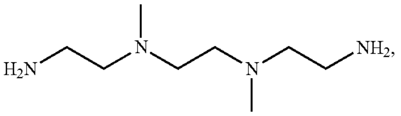

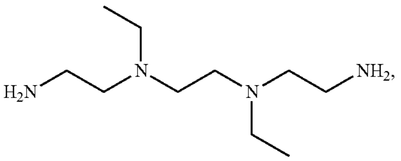

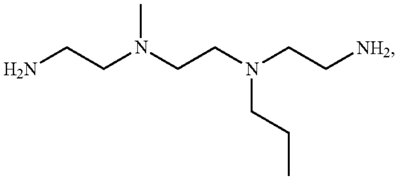

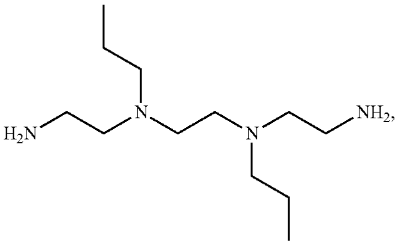

-continued

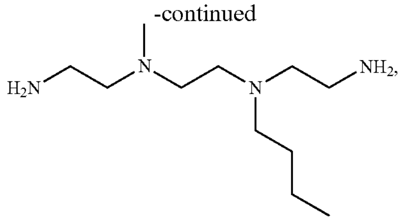

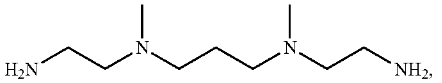

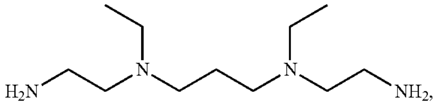

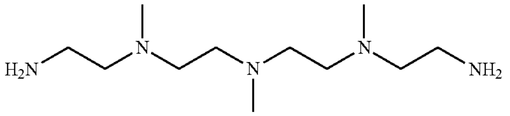

or

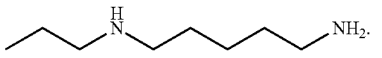

In some embodiments, the ketal-containing acrylate $CH_2{=}CH{-}C(O)O{-}R_2{-}Y{-}R_3{-}Z{-}R_4$ is

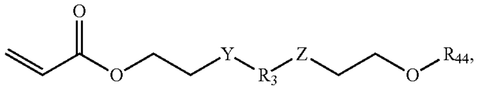

and the remaining variables are as defined for formula (I).

In some embodiments, the reaction is an addition reaction, preferably a Michael addition reaction.

In some embodiments, the reaction is carried out at a temperature of 60-85° C., such as at 70° C. for 24-96 hours or longer.

The ketal-containing acrylate described in the present invention can be synthesized according to a method known in the art, such as a method disclosed in CN 110101665 A. The ketal (thioketone)-containing acrylate is an ester compound obtained by subjecting an acrylic acid and an alcohol compound containing ketal (thioketone) to an esterification reaction.

Other lipids of the present invention can be prepared by the above synthesis routes and other routes known in the art using other suitable starting materials. The methods listed above may include one or more additional steps to add or remove appropriate protecting groups to finally allow for the synthesis of lipids. In addition, various synthesis steps can be carried out in an alternative order or sequence to obtain the desired materials. Synthetic chemical transformation and protective group methods (protection and deprotection) which can be used to synthesize suitable lipids are known in the art.

In a third aspect, the present invention provides a pharmaceutical composition comprising a pharmaceutical carrier and a lipid nanoparticle (LNP), wherein the lipid nanoparticle comprises the lipid of formula (I) according to the present invention and a pharmaceutically active molecule.

In some embodiments, the pharmaceutically active molecule is a small molecule drug, a protein, a peptide, a nucleic acid, a saccharide, or a combination thereof. In a further embodiment, the pharmaceutically active molecule is an mRNA. In still a further embodiment, the mRNA may be a firefly luciferase mRNA which can be expressed as luciferase.

In some embodiments, the lipid nanoparticle has a particle size distribution of 50 to 500 nm.

In some embodiments, the lipid and the pharmaceutically active molecule are bound via a non-covalent interaction, a covalent bond or both.

In some embodiments, the lipid nanoparticle further comprises other lipids selected from cholesterol, dioleoylphosphatidylethanolamine (DOPE, CAS: 4004-05-1), and distearoylphosphatidylethanolamine-polyethylene glycol 2000 (DSPE-PEG2000, CAS: 147867-65-0), or 1,2-dimyristoyl-RAC-glycero-3-methoxy polyethylene glycol 2000 (DMG-PEG2000, CAS: 160743-62-4), or a combination thereof. Furthermore, replacing DOPE with the same ratio of 1,2-dioleoyl-sn-glycero-3-phosphocholine (DOPC, CAS: 4235-95-4) or distearoyl phosphatidylcholine (DSPC, CAS: 816-94-4) can also achieve similar delivery effects. In a further embodiment, the lipid nanoparticles further contain cholesterol, dioleoylphosphatidylethanolamine, and distearoylphosphatidylethanolamine-polyethylene glycol 2000 or 1,2-dimyristoyl-RAC-glycero-3-methoxy polyethylene glycol 2000. The molar ratio of lipid:cholesterol:DOPE:DSPE-PEG2000 in the examples of the present invention is 50:38.5:10:1.5.

In some embodiments, the lipid nanoparticles of the present invention are prepared by the method comprising: dissolving the ionizable lipid compound of the present invention, cholesterol, DOPE and DSPE-PEG2000 in absolute ethanol, and dissolving the pharmaceutically active molecule (the mass of lipids being 5-20 times the mass thereof (the N/P ratio of lipids to nucleic acids being in the range of 5:1-20:1)) in 100 mM sodium acetate buffer (pH=5.2). The ethanol solution and the sodium acetate buffer solution were mixed and prepared on a microfluidic machine at a flow rate of 1:3. In a further embodiment, the pharmaceutically active molecule is an mRNA.

In a fourth aspect, the present invention relates to a method for regulating gene expression comprising delivering a nucleic acid to a cell, the method comprising: contacting the cell with the pharmaceutical composition of the third aspect under conditions sufficient to cause uptake of the nucleic acid into the cell. In some embodiments, the cell is contacted in vitro or ex vivo. In some embodiments, the cell is contacted in vivo. In some embodiments, the regulation of gene expression is sufficient to treat a disease or condition, such as cancer.

The present invention also relates to a method of treating a disease or condition in a patient, the method comprising administering to a patient in need thereof a pharmaceutically effective amount of the pharmaceutical composition described in the present application, wherein the pharmaceutical composition comprises a therapeutic nucleic acid or protein for the disease or condition.

Definitions

The term "aliphatic group" refers to a saturated or unsaturated, linear or branched, acyclic, cyclic or polycyclic hydrocarbon moiety. Examples include, but are not limited to, alkyl, alkenyl, alkynyl, cycloalkyl, cycloalkenyl, and cycloalkynyl moieties.

The term "alkyl" includes hydrocarbon groups selected from linear and branched saturated hydrocarbon groups containing 1 to 30, such as 1 to 24, 1 to 18, such as 1 to 12, further such as 1 to 10, and still further such as 1 to 8 or 1 to 6 or 1 to 4 carbon atoms. Examples of monovalent alkyl or alkyl include, but are not limited to, methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosyl, triacontyl, etc. Examples of divalent alkyl, i.e. alkylene, include, but are not limited to, methylene, ethylene, propylene, butylene, pentylene, hexylene, heptylene, octylene, nonylene, decylene, undecylene, dodecylene, tridecylene, tetradecylene, pentadecylene, hexadecylene, heptadecylene, octadecylene, nonadecylene, eicosylene, triacotylene, etc.

A monovalent group is a group formed by removing a hydrogen atom from the corresponding hydrocarbon moiety. A divalent group is a group formed by removing two hydrogen atoms from the corresponding hydrocarbon moiety.

The term "alkenyl" includes hydrocarbon groups selected from linear and branched hydrocarbon groups containing at least one C═C double bond and 2 to 30, such as 2 to 24, 2 to 18, such as 2 to 8, further such as 2 to 6 carbon atoms. Examples of alkenyl, such as C2-6 alkenyl, include, but are not limited to, ethenyl/vinyl, prop-1-enyl, prop-2-enyl, 2-methylprop-1-enyl, but-1-enyl, but-2-enyl, but-3-enyl, buta-1,3-dienyl, 2-methylbuta-1,3-dienyl, hex-1-enyl, hex-2-enyl, hex-3-enyl, hex-4-enyl, hexa-1,3-dienyl, dodecenyl, tetradecenyl, hexadecenyl, octadecenyl, etc.

The term "alkynyl" includes hydrocarbon groups selected from linear and branched hydrocarbon groups containing at least one C═C triple bond and 2 to 30, such as 2 to 24, 2 to 18, such as 2 to 8, further such as 2 to 6 carbon atoms. Examples of alkynyl, such as C2-6 alkynyl, include but are not limited to ethynyl, 1-propynyl, 2-propynyl (propargyl), 1-butynyl, 2-butynyl, and 3-butynyl.

The term "cycloalkyl" includes hydrocarbon groups selected from saturated cyclic hydrocarbon groups containing monocyclic and polycyclic (e.g., bicyclic and tricyclic) groups, including fused, bridged or spirocyclic alkyl. The cycloalkyl may contain 3 to 30, 3 to 12, for example 3 to 10, further for example 3 to 8, further for example 3 to 6, 3 to 5 or 3 to 4 carbon atoms. Furthermore, by way of example, the cycloalkyl may be selected from monocyclic groups containing 3 to 12, such as 3 to 10, further such as 3 to 8, 3 to 6 carbon atoms. Examples of monocyclic cycloalkyl include cyclopropyl, cyclobutyl, cyclopentyl, cyclohexyl, cycloheptyl, cyclooctyl, cyclononyl, cyclodecyl, cycloundecyl, and cyclododecyl. The term "cycloalkenyl" refers to a non-aromatic, cyclic hydrocarbon moiety containing at least one double bond, such as cyclohexenyl and cyclohexenylene. The term "cycloalkynyl" refers to a non-aromatic, cyclic hydrocarbon moiety containing at least one triple bond, such as cyclooctynyl and cyclooctynylene. Similarly, cycloalkylene, cycloalkenylene, and cycloalkynylene are corresponding divalent groups.

The term "heteroaliphatic group" refers to an aliphatic moiety containing at least one heteroatom selected from N, O, P, B, S, Si, Sb, Al, Sn, As, Se, and Ge. The heteroaliphatic group of the present invention includes alkyl, alkenyl or alkynyl containing at least one heteroatom selected from N, O, P, B, S, Si, Sb, Al, Sn, As, Se, and Ge, and a cycloalkyl, cycloalkenyl or cycloalkynyl moiety containing at least one heteroatom selected from N, O, P, B, S, Si, Sb, Al, Sn, As, Se, and Ge. The cyclic heteroaliphatic group includes a 3- to 7-membered monocyclic heteroaliphatic group and a 7- to 12-membered bicyclic heteroaliphatic group, and the cyclic heteroaliphatic groups contain 1-3 or more, for example, 1-3 heteroatoms selected from oxygen, nitrogen and sulfur. In some embodiments, the cyclic heteroaliphatic group is a 3- to 7-membered monocyclic heteroaliphatic group containing 1-3 heteroatoms selected from oxygen, nitrogen and sulfur. Cyclic heteroaliphatic groups include, but are not limited to, pyrrolidinyl, imidazolidinyl, piperidinyl, piperazinyl, pyranyl, morpholinyl, oxiranyl, azirinyl, thiiranyl, azetidinyl, oxetanyl, thietanyl, dithietanyl, dihydropyridine, tetrahydropyridine, thiomorpholine, homopiperazinyl, homopiperidinyl, azepanyl, oxepanyl, thiepanyl, oxathianyl, dioxepanyl, oxathiepanyl, oxazepanyl, dithiepanyl, thiazepanyl, diazepanyl, thiazinanyl, oxazepine, diazepine, thiazepine, dihydrothienyl, dihydropyranyl, dihydrofuranyl, tetrahydrofuranyl, tetrahydrothienyl, tetrahydropyranyl, tetrahy drothiapyranyl, pyrrolinyl, indolinyl, dioxanyl, dioxolanyl, pyrazolinyl, pyrazolidinyl, dithianyl, dithiolanyl, pyrimidonyl, dioxo-thiomorpholinyl, azabicyclo[3.1.0]hexyl, azabicyclo[4.1.0]heptyl, azabicyclo[2.2.2]hexyl, etc. A typical heteroaliphatic group is heteroalkyl, i.e. an alkyl group containing at least one heteroatom such as N, O or S, e.g. $C_{1-6}$ alkyl containing one N atom, $C_{1-6}$ alkyl containing one O atom, or $C_{1-6}$ alkyl containing one S atom; or $C_{1-4}$ heteroalkyl containing one N atom, $C_{1-4}$ heteroalkyl containing one O atom, or $C_{1-4}$ heteroalkyl containing one S atom.

The term "oxyaliphatic group" refers to a —O-aliphatic group. Examples of the oxyaliphatic group include methoxy, ethoxy, n-propoxy, isopropoxy, n-butoxy, isobutoxy, sec-butoxy, and tert-butoxy.

The term "aryl (aromatic group)" refers to a C6 monocyclic, C10 bicyclic, C14 tricyclic, C20 tetracyclic, or C24 pentacyclic aromatic ring system. Examples of aryl include phenyl, phenylene, naphthyl, naphthylene, anthryl, anthrylene, pyrenyl, and pyrenylene.

The term "heteroaryl (heteroaromatic group)" refers to aromatic 5- to 8-membered monocyclic, 8- to 12-membered bicyclic, 11- to 14-membered tricyclic, and 15- to 20-membered tetracyclic ring systems having one or more heteroatoms (such as O, N, S, or Se). Examples of heteroaryl include furanyl, furanylene, fluorenyl, fluorenylene, pyrrolyl, pyrrolylene, thienyl, thienylene, oxazolyl, azolylene, imidazolyl, imidazolylene, benzimidazolyl, benzimidazolylene, thiazolyl, thiazolylene, pyridyl, pyridylene, pyrimidinyl, pyrimidinylene, quinazolinyl, quinazolinylene, quinolinyl, quinolinylene, isoquinolinyl, isoquinolinylene, indolyl, and indolylene.

Unless otherwise specified, the aliphatic group, heteroaliphatic group, oxyaliphatic group, alkyl, alkylene, alkenyl, alkenylene, alkynyl, alkynylene, cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl mentioned in the present application include both substituted and unsubstituted moieties. Possible substituents on the cycloalkyl, cycloalkylene, cycloalkenyl, cycloalkenylene, cycloalkynyl, cycloalkynylene, heterocycloalkyl, heterocycloalkylene, heterocycloalkenyl, heterocycloalkenylene, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_2$-$C_{20}$ heterocycloalkyl, $C_3$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_2$-$C_{20}$ dialkylamino, arylamino, diarylamino, $C_1$-$C_{10}$ alkylsulfonamido, arylsulfonamido, $C_1$-$C_{10}$ alkylimino, arylimino, $C_1$-$C_{10}$ alkylsulfonimido, arylsulfonimido, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amido, amidino, guanidine, ureido, thioureido, cyano, nitro, nitroso, azido, acyl, thioacyl, acyloxy, carboxyl, and carboxylate. In another aspect, possible substituents on the aliphatic group, heteroaliphatic group, oxyaliphatic group, alkyl, alkylene, alkenyl, alkenylene, alkynyl, and alkynylene include all the substituents listed above, except $C_1$-$C_{10}$ alkyl. Cycloalkyl, cycloalkylene, cycloalkenyl, cycloalkenylene, heterocycloalkyl, heterocycloalkylene, heterocycloalkenyl, heterocycloalkenylene, aryl, and heteroaryl may also be fused with one another.

The term "pharmaceutically active molecule" refers to any chemical substance intended for medical diagnosis, cure, treatment or prevention of diseases, including small molecule drugs such as chemotherapeutic drugs, and macromolecule drugs such as oligopeptides, oligosaccharides, oligonucleotides, peptides, proteins or nucleic acids.

DETAILED DESCRIPTION OF EMBODIMENTS

Figure 1A:
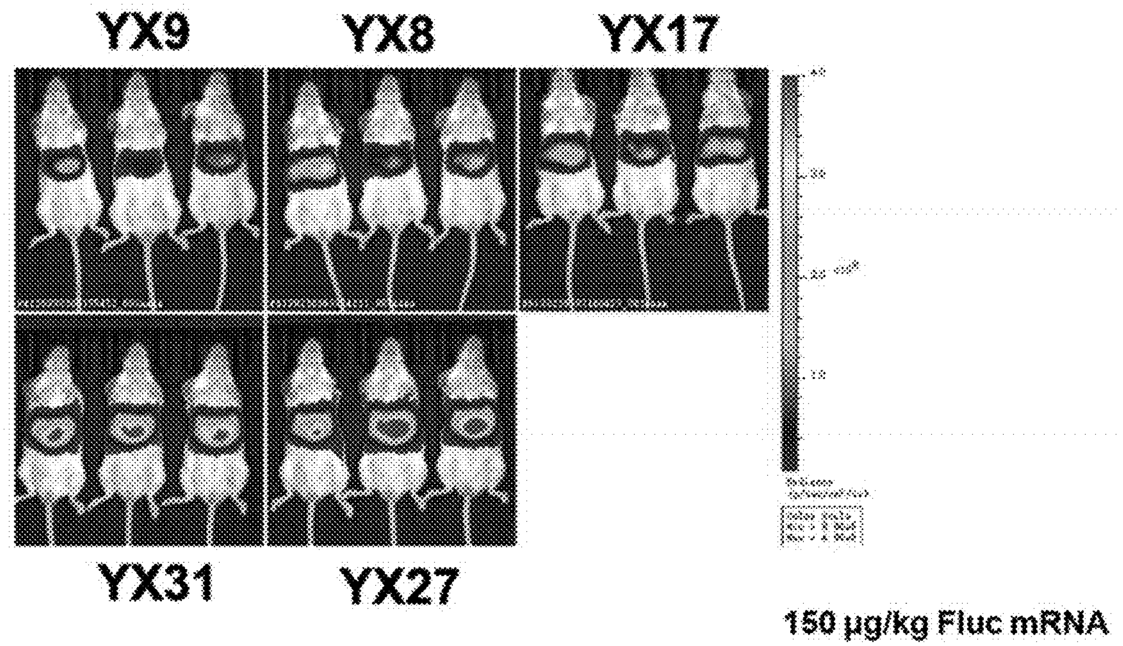
FIG. 1A shows whole-body bioluminescence imaging (in vivo imaging system, IVIS) 6 hours after delivery of firefly luciferase (Fluc) mRNAs by LNPs containing lipid compounds with different hydrophobic chain lengths, where mice were administered via tail vein (dose: 150 μg/kg).
Figure 1B:
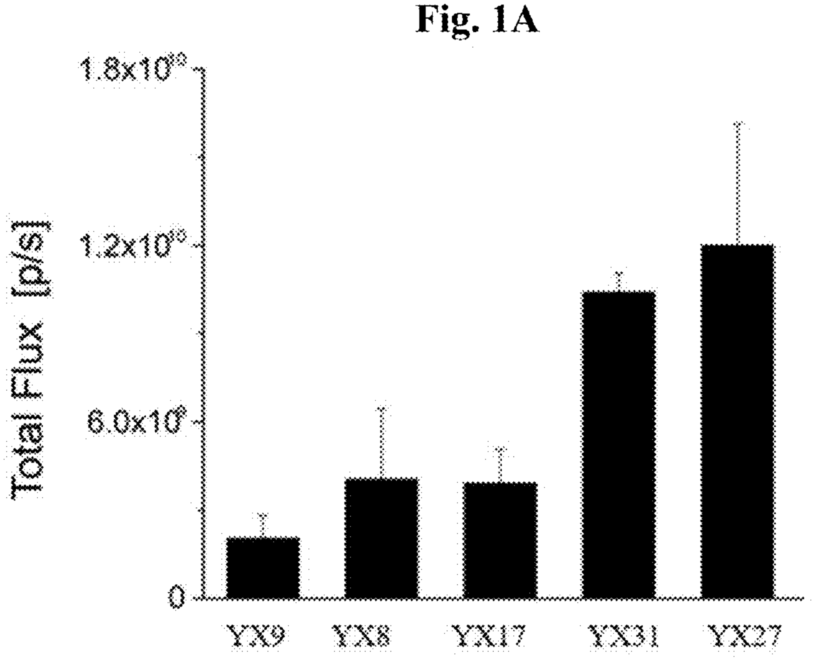
FIG. 1B shows the expression level of luciferase and bioluminescence intensity in liver tissue.
Figure 2A:
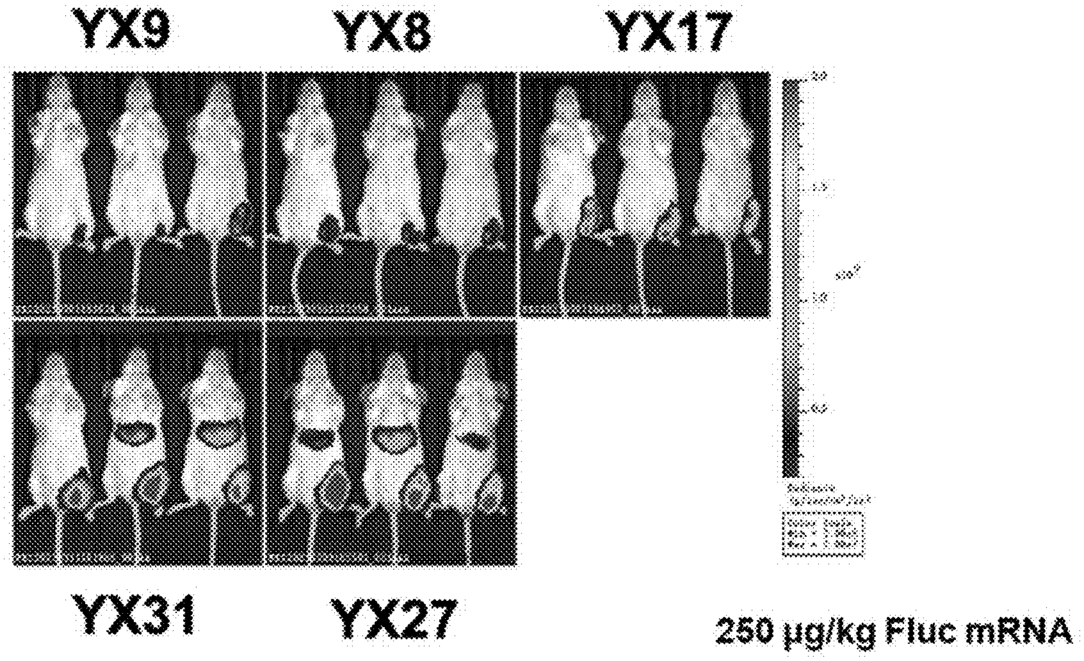
FIG. 2*a* shows whole-body bioluminescence imaging (in vivo imaging system, IVIS) 6 hours after delivery of firefly luciferase mRNAs by LNPs containing lipids with different chain lengths, where mice were administered intramuscularly (dose: 250 μg/kg).
Figure 2B:
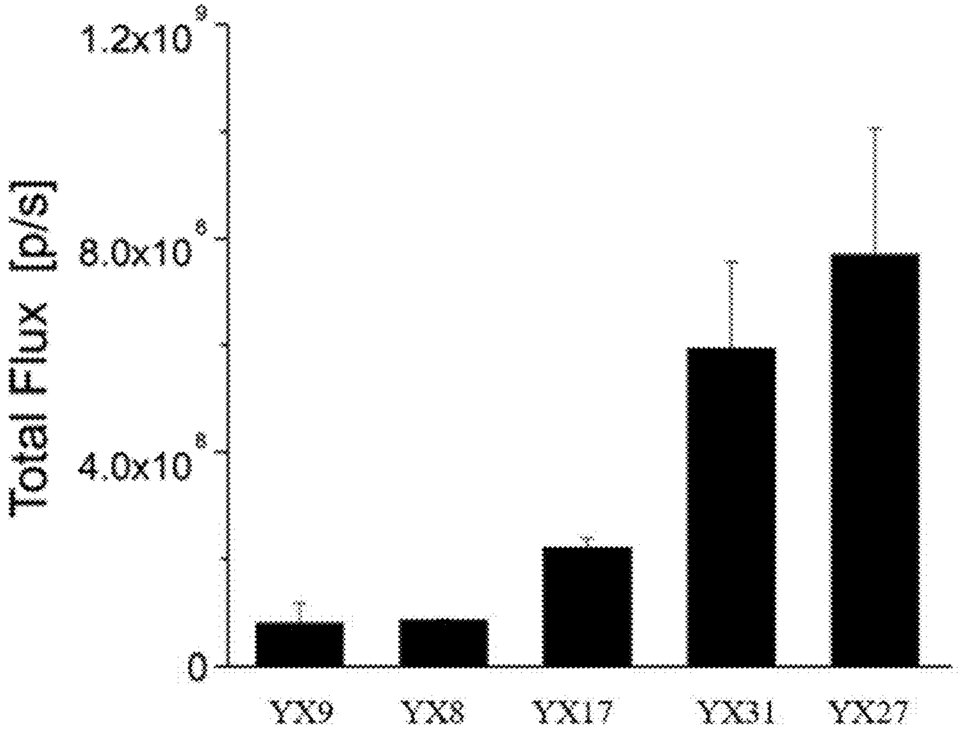
FIG. 2B shows the expression level of luciferase and bioluminescence intensity at tissue level.

The present invention will be further described in detail in conjunction with specific embodiments, and examples are given only to illustrate the present invention, but not to limit the scope of the present invention. The examples provided below can be used as a guide for further improvement by those of ordinary skill in the art and are not intended to limit the present invention in any way.

For all the quantitative experiments in the following examples, three repeated experiments are set up and the results are averaged.

The experimental methods in the following examples are all conventional unless otherwise specified. The materials, reagents, etc., used in the following examples can all be obtained from commercial sources unless otherwise specified.

In the following examples, cholesterol is a product from Macklin, with article number C10006595, CAS: 57-88-5.

In the following examples, both DOPE (dioleoylphosphatidylethanolamine, CAS: 4004-05-1) and DMG-$PEG_{2000}$ (CAS: 147867-65-) are products from Aveto (Shanghai) Pharmaceutical Technology Co., Ltd.

The firefly luciferase mRNA in the following examples is a product from Shanghai Hongene Technology Development Co., Ltd.

In the following examples, Balb/c mice are products from Beijing Vital River Laboratory Animal Technology Co., Ltd.

EXAMPLES

Example 1: Synthesis of Ionizable Lipid Compounds

An ionizable lipid compound was synthesized by a Michael addition reaction between a corresponding hydrophilic amine compound and a corresponding hydrophobic tail, wherein the hydrophobic tail was a ketal-containing acrylate, specifically a thioketal-containing acrylate.

Hydrophobic tail compound TK is synthesized or prepared as follows:

TK12 is 2-((2-((2-(dodecyloxy)ethyl)thio)propan-2-yl)thio)ethyl acrylate

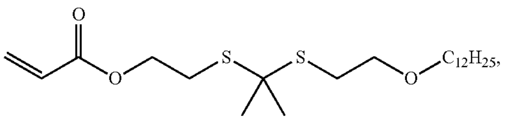

i.e. the compound of formula I-1 in Example 2 of CN110101665A, and $^1$H NMR of TK-12 was: $^1$H NMR (300 MHz, $CDCl_3$) δ 6.18 (s, 1H), 5.97 (d, J=10.2 Hz, 1H), 4.26 (s, 2H), 3.51 (s, 4H), 3.34 (s, 6H), 2.87 (s, 1H), 2.74 (s, 1H), 1.55 (s, 4H), 1.50-1.39 (m, 1H), 1.25 (s, 6H), 0.86 (s, 1H).

TK2, TK4, TK6, TK8, and TK10 were synthesized in a manner similar to that in Examples 1 and 2 of CN110101665A, using

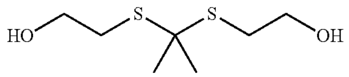

2,2'-(propane-2,2-diylbis(sulfanediyl))bis(ethan-1-ol) and a corresponding short-chain haloalkane Halo-$C_uH_{2u\ 1}$ as starting materials to prepare

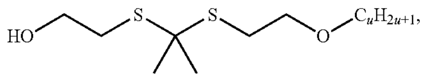

which was then reacted with acryloyl halide (such as acryloyl chloride) to obtain the corresponding TK2, TK4, TK6, TK8 and TK10, in which TK10 is 2-((2-((2-(decyloxy)ethyl)thio)propan-2-yl)thio)ethyl acrylate

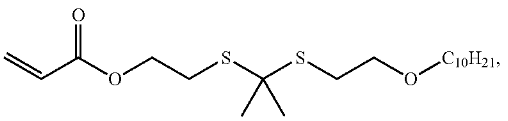

and $^1$H NMR of TK10 was as follows: $^1$H NMR (300 MHz, $CDCl_3$) δ 6.45 (d, 1H), 6.13 (m, 1H), 5.86 (d, 1H), 4.31 (t, 2H), 3.58 (t, 2H), 3.43 (t, 2H), 2.91 (t, 2H), 2.82 (t, 2H), 1.61-1.26 (m, 23H), 0.87 (t, 3H).

TK8 is 2-((2-((2-(octyloxy)ethyl)thio)propan-2-yl)thio)ethyl acrylate

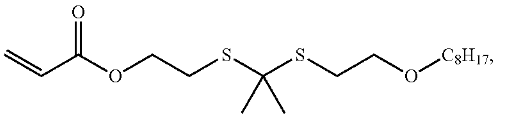

and $^1$H NMR of TK8 was as follows: $^1$H NMR (300 MHz, $CDCl_3$) δ 6.40 (d, 1H), 6.13 (m, 1H), 5.86 (d, 1H), 4.31 (t, 2H), 3.58 (t, 2H), 3.43 (t, 2H), 2.91 (t, 2H), 2.82 (t, 2H), 1.61-1.27 (m, 17H), 0.87 (t, 3H).

TK6 is 2-((2-((2-(hexyloxy)ethyl)thio)propan-2-yl)thio)ethyl acrylate

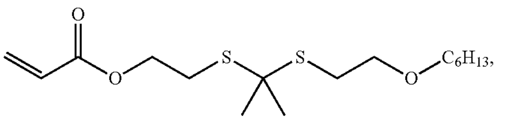

and $^1$H NMR of TK6 was as follows: $^1$H NMR (300 MHz, $CDCl_3$) δ 6.41 (d, 1H), 6.12 (m, 1H), 5.83 (d, 1H), 4.32 (t, 2H), 3.59 (t, 2H), 3.46 (t, 2H), 2.92 (t, 2H), 2.82 (t, 2H), 1.61 (m, 8H), 1.31 (m, 6H), 0.88 (t, 3H).

TK4 is 2-((2-((2-(butyloxy)ethyl)thio)propan-2-yl)thio)ethyl acrylate

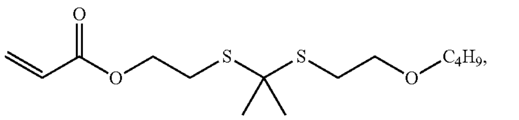

and $^1$H NMR of TK4 was as follows: $^1$H NMR (300 MHz, $CDCl_3$) δ 6.41 (d, 1H), 6.12 (t, 1H), 5.83 (d, 1H), 4.32 (d, 2H), 3.59 (d, 2H), 3.46 (d, 2H), 2.92 (d, 2H), 2.82 (d, 2H), 1.61-1.38 (m, 10H), 0.89 (d, 3H).

The synthesis of the ionizable lipid compound YX of the present invention can be found in CN110101665A, etc.

YX9, i.e. the compound of formula II-10 in Example 5 of CN110101665A, was synthesized from the hydrophilic amine compound 3,3'-diamino-N-methyldipropylamine (CAS: 105-83-9) and TK12 in a similar manner to the method in Example 5 of CN110101665A, except that the molar ratio of the hydrophilic amine compound to TK12 was 4.3:1. $^1$H NMR of YX9 was as follows: $^1$H NMR (300 MHz, $CDCl_3$) δ 4.21 (t, 8H), 3.57 (t, 8H), 3.42 (t, 8H), 2.85-2.76 (m, 24H), 2.44 (t, 12H), 2.29 (s, 4H), 2.18 (s, 3H), 1.59-1.25 (m, 114H), 0.87 (t, 12H).

YX8 was synthesized from hydrophilic amine compound 3,3'-diamino-N-methyldipropylamine and TK10, wherein the hydrophilic amine compound 3,3'-diamino-N-methyldipropylamine and TK10 were mixed at a molar ratio of 4.3:1 and heated at 70° C. for 72 h. The crude product was purified on a silica gel column with dichloromethane/methanol as an eluent to obtain ionizable lipid compound YX8. $^1$H NMR of YX8 was as follows: $^1$H NMR (300 MHz, $CDCl_3$) δ 4.21 (t, 8H), 3.57 (t, 8H), 3.42 (t, 8H), 2.85-2.76 (m, 24H), 2.44 (t, 12H), 2.28 (s, 4H), 2.19 (s, 3H), 1.60-1.25 (m, 100H), 0.87 (t, 12H).

YX17, YX27 and YX31 were synthesized by mixing hydrophilic amine compound 3,3'-diamino-N-methyldipropylamine with a corresponding hydrophobic tail compound at a molar ratio of 4.3:1.

$^1$H NMR of YX17 was as follows: $^1$H NMR (300 MHz, $CDCl_3$) δ 4.21 (t, 8H), 3.58 (t, 8H), 3.43 (t, 8H), 2.85-2.77 (m, 24H), 2.45 (m, 12H), 2.28 (s, 4H), 2.18 (s, 3H), 1.60-1.28 (m, 83H), 0.87 (t, 12).

$^1$H NMR of YX27 was as follows: $^1$H NMR (300 MHz, $CDCl_3$) δ 4.22 (t, 8H), 3.58 (t, 8H), 3.44 (t, 8H), 2.86-2.77 (m, 24H), 2.45 (t, 12H), 2.28 (t, 4H), 2.18 (s, 3H), 1.60-1.38 (m, 45H), 0.92 (t, 12H).

$^1$H NMR of YX31 was as follows: $^1$H NMR (300 MHz, $CDCl_3$) δ 4.22 (t, 8H), 3.58 (t, 8H), 3.43 (t, 8H), 2.86-2.77 (m, 24H), 2.45 (t, 12H), 2.28 (t, 4H), 2.18 (s, 3H), 1.60 (m, 37H), 1.29 (s, 25H), 0.88 (t, 12H).

YX9

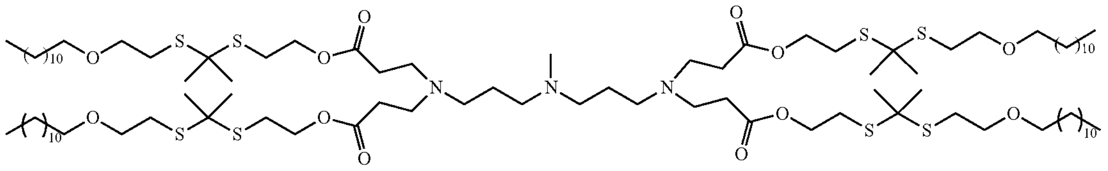

YX8

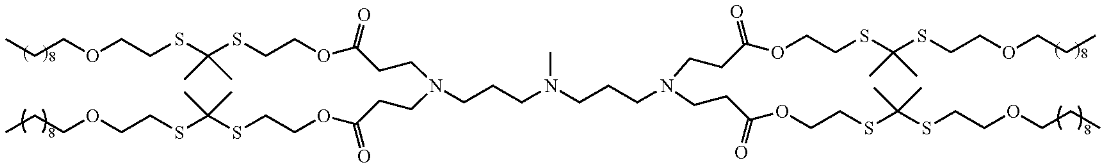

YX17

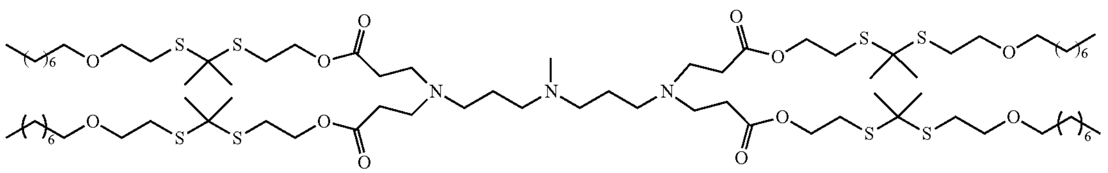

-continued

YX31

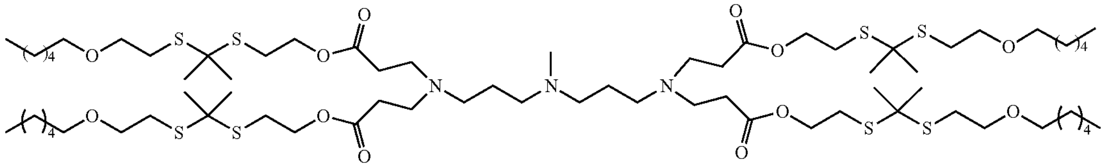

YX27

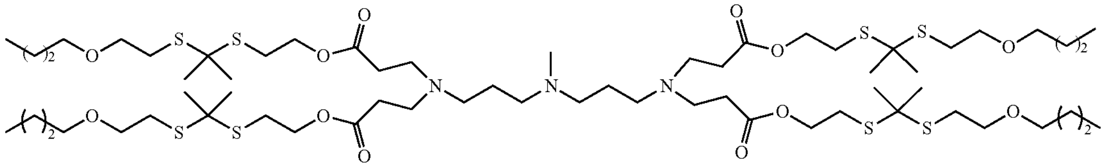

Ionizable lipid compounds YX28, YX35, YX29 and YX33 were synthesized from hydrophilic amine compound N-methyl-2,2-diaminodiethylamine (CAS No. 4097-88-5) or N,N'-bis(2-aminoethyl)-N,N'-dimethyl-1,3-propanediamine (CAS No. 152829-22-6) and corresponding hydrophobic tail compounds, in a manner similar to the above.

$^1$H NMR of YX28 was as follows: $^1$H NMR (300 MHz, $CDCl_3$) δ 4.22 (t, 8H), 3.58 (t, 8H), 3.44 (t, 8H), 2.86-2.77 (m, 24H), 2.55-2.46 (m, 16H), 2.23 (s, 3H), 1.60-1.38 (m, 41H), 0.91 (t, 12H).

$^1$H NMR of YX29 was as follows: $^1$H NMR (300 MHz, $CDCl_3$) δ 4.22 (t, 8H), 3.58 (t, 8H), 3.44 (t, 8H), 2.86-2.77 (m, 24H), 2.56 (t, 4H), 2.46 (t, 12H), 2.34 (t, 4H), 2.22 (s, 6H), 1.6-1.38 (m, 50H), 0.92 (t, 12H).

$^1$H NMR of YX33 was as follows: $^1$H NMR (300 MHz, $CDCl_3$) δ 4.22 (t, 8H), 3.58 (t, 8H), 3.43 (t, 8H), 2.86-2.77 (m, 24H), 2.57 (s, 4H), 2.46 (t, 12H), 2.35 (s, 4H), 2.23 (s, 6H), 1.60-1.29 (m, 60H), 0.88 (t, 12H).

$^1$H NMR of YX35 was as follows: $^1$H NMR (300 MHz, $CDCl_3$) δ 4.22 (t, 8H), 3.58 (t, 8H), 3.43 (t, 8H), 2.86-2.77 (m, 24H), 2.55-2.46 (m, 16H), 2.23 (s, 3H), 1.60 (m, 35H), 1.29 (m, 24H), 0.89 (t, 12H).

YX28

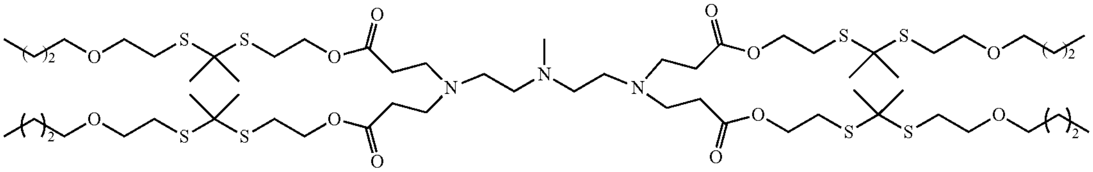

YX35

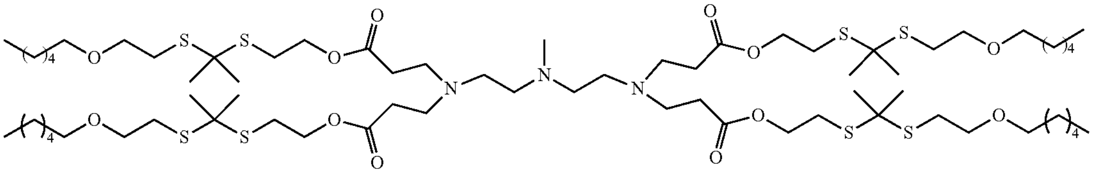

YX29

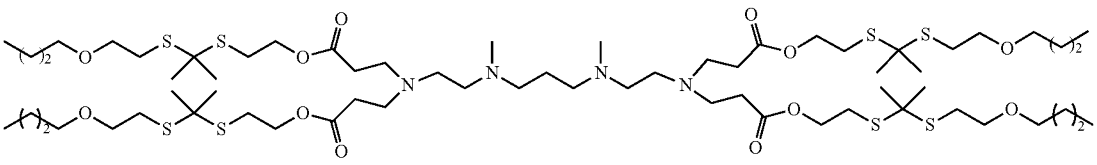

YX33

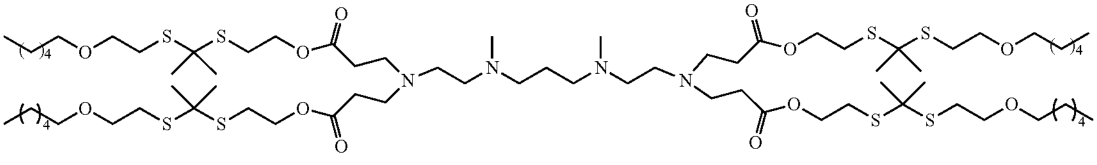

Example 2: Encapsulation of Firefly Luciferase mRNAs and Preparation of Lipid Nanoparticles In order to achieve mRNA delivery at animal level, the inventors prepared mRNA/lipid nanoparticles using the method as follows: formulating each of the ionizable lipid compounds (YX8, YX17, YX31, YX27, YX28, YX35, YX29 or YX33) prepared in Example 1, cholesterol, DOPE and DMG-PEG2000 into a 10 mg/mL ethanol solution. Taking YX27 as an example, when preparing an mRNA/LNP complex in a single time, YX27 solution (1.6 mg) was measured and mixed with cholesterol, DOPE and DMG-PEG2000 according to a molar ratio of 50:38.5:10:1.5, and the total volume of the solution was allowed to reach 450 μl by supplementing ethanol. 150 μg of firefly luciferase mRNAs were taken and added to a sodium acetate buffer (50 mM, pH=5.2), and the total volume of the solution was 1350 μl. The ionizable lipid compound solution and the mRNA solution were mixed by introducing into a microfluidic machine (speed: 0.2 mL/min of ethanol solution, and 0.6 mL/min of sodium acetate buffer solution) to prepare lipid nanoparticles encapsulating mRNAs, which were dialyzed against PBS buffer for 2 hours, and the obtained samples were directly used for animal experiments. The ratio of the ionizable lipid compound YX27 to mRNAs was calculated according to the molar ratio (N/P) of the nitrogen atoms in YX27 to the phosphorus atoms in the phosphate skeleton of the mRNAs. In this example, N/P was 7.5.

For lipid nanoparticles encapsulating mRNAs, Quant-It™ RiboGreen RNA Assay Kit (ThermoFisher Scientific, USA) was used to determine the concentration of free RNAs therein, and on this basis, a method for determining the RNA encapsulation efficiency of the nanoparticle composition was established. Samples were diluted in TE buffer (Solarbio, T1120, pH 8.0) to a concentration of about 5 μg/mL. 50 μL of the diluted sample was transferred to a polystyrene 96-well plate and 50 μL of TE buffer or 50 μL of 2% Triton X-100 solution (Solarbio, T8200) was added to the wells. The plate was incubated at a temperature of 37° C. for 10 minutes. Reagents were diluted 1:200 in TE buffer and 100 μL of this solution was added to each well. The fluorescence intensity can be measured using a fluorescence plate reader (BIOTEK/Synergy H1) at an excitation wavelength of 480 nm and an emission wavelength of 520 nm, and the percentage of free RNAs was determined by dividing the fluorescence intensity of the intact sample (without addition of Triton X-100) by the fluorescence value of the lysed sample (caused by addition of Triton X-100).

The LNP comprising YX27 in this example was tested as follows: an average particle size of 185 nm, PDI of 0.148, and a zeta potential of −7.87 mV.

Example 3: Animal Experiment of Delivery of mRNAs by Lipid Nanoparticles of the Resent Invention In order to verify the delivery effect of the above Fluc mRNA/LNP preparation, YX27 LNPs encapsulating 150 μg/kg Fluc mRNAs were injected into 6-8 week-old female Balb/c mice by administration via tail vein, or YX27 LNPs encapsulating 250 μg/kg Fluc mRNAs were injected into the hind legs of mice by intramuscular administration; after 6 hours, 200 μl of D-Lucifin (with a mass fraction of 30%) was injected by intraperitoneal administration, and the expression and intensity of luciferase in the whole body, liver and muscle administration sites were detected by PerkinElmer IVIS Lumina III small animal in vivo optical imaging system. In order to study the effect of the hydrophobic chain length of lipid compounds on mRNA delivery efficiency, LNP samples encapsulating Fluc mRNAs were prepared using lipid compounds YX9, YX8, YX17 and YX31 respectively according to YX27 experimental operation, and the efficiency of luciferase expression in mice was studied. The study found that the mRNA delivery efficiency of the lipid compounds containing 4 and 6 carbon atoms at hydrophobic carbon chain tail structures was significantly superior to other lipid molecules.

The results of in vivo luciferase imaging luminescence intensity after using different lipid compounds to deliver Fluc mRNAs were shown in the table below and FIG. 1A, FIG. 1B, FIG. 2A and FIG. 2B:

| Lipid No. | Average intensity | Standard deviation | Average intensity | Standard deviation |
|---|---|---|---|---|
| | Administration via tail vein/liver luminescence intensity | | Intramuscular administration/muscle luminescence intensity | |
| YX9 | 2.04E+09 | 7.83E+08 | 7.85E+07 | 3.79E+07 |
| YX8 | 4.04E+09 | 2.42E+09 | 8.42E+07 | 2.93E+06 |
| YX17 | 3.91E+09 | 1.16E+09 | 2.20E+08 | 1.74E+07 |
| YX31 | 1.04E+10 | 6.7E+08 | 7.70E+08 | 2.36E+08 |
| YX27 | 1.2E+10 | 4.13E+09 | 5.93E+08 | 1.62E+08 |

Unit: p/s

Example 4: Effect of the N/P Ratio of YX27 Dosage Forms on mRNA Delivery

Figure 3:
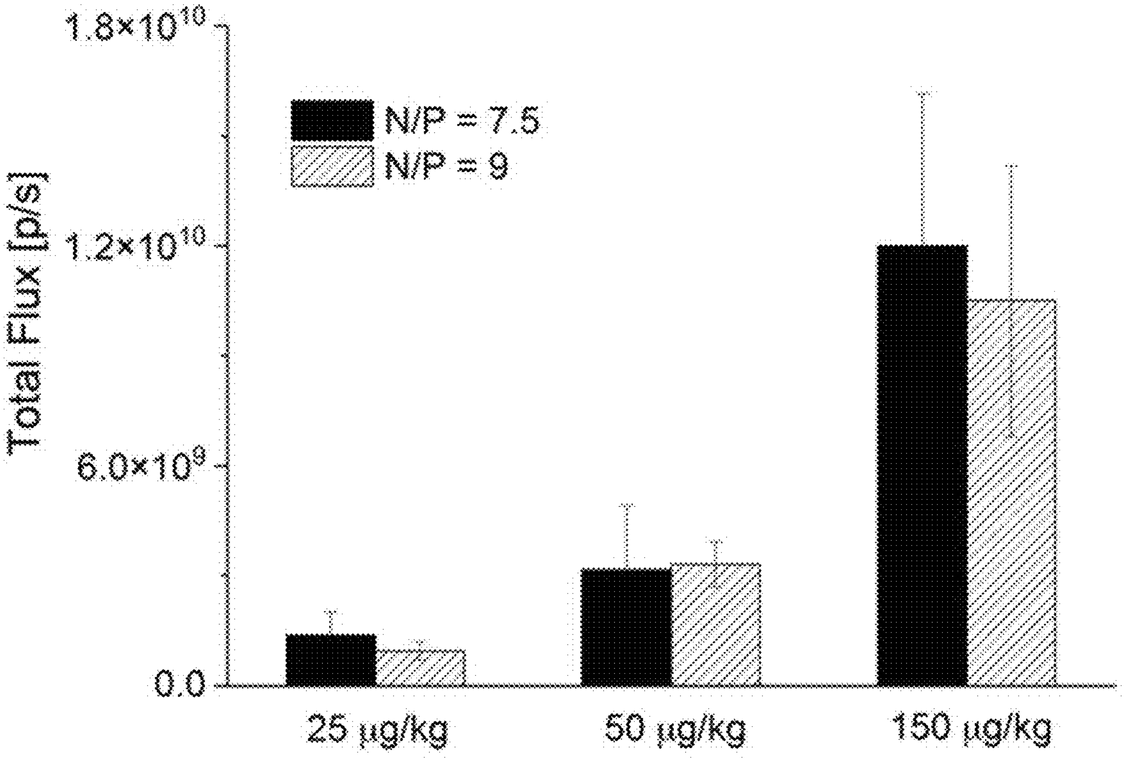
FIG. 3 shows the expression level of luciferase and bioluminescence intensity in liver tissue 6 hours after delivery of firefly luciferase mRNAs by YX27 lipid nanoparticles under different N/P conditions, where mice were administered via tail vein (dose: 150 μg/kg).

In order to study the effect of the mixing ratio (N/P ratio) of ionizable lipids and mRNAs as the LNP components on the mRNA delivery efficiency, mixed samples of YX27 and luciferase mRNAs at N/P ratios of 7.5 and 9 were prepared according to the operation steps of Example 2, the mRNA delivery and the expression and intensity of luciferase in the whole body, liver and other sites were studied by administration via tail vein (the delivery results are shown in FIG. 3 and the table below).

| Fluc mRNA dose | Average intensity | Standard deviation | Average intensity | Standard deviation |
|---|---|---|---|---|
| | N/P = 7.5 | | N/P = 9 | |
| 25 μg/kg | 1.37E+09 | 6.29E+08 | 9.54E+08 | 2.49E+08 |
| 50 μg/kg | 3.15E+09 | 1.76E+09 | 3.29E+09 | 6.17E+08 |
| 150 μg/kg | 1.20E+10 | 4.15E+09 | 1.05E+10 | 3.69E+09 |

Example 5: Comparing the Effect of YX27 with SM102 and MC3 on mRNA Delivery

Figure 4A:
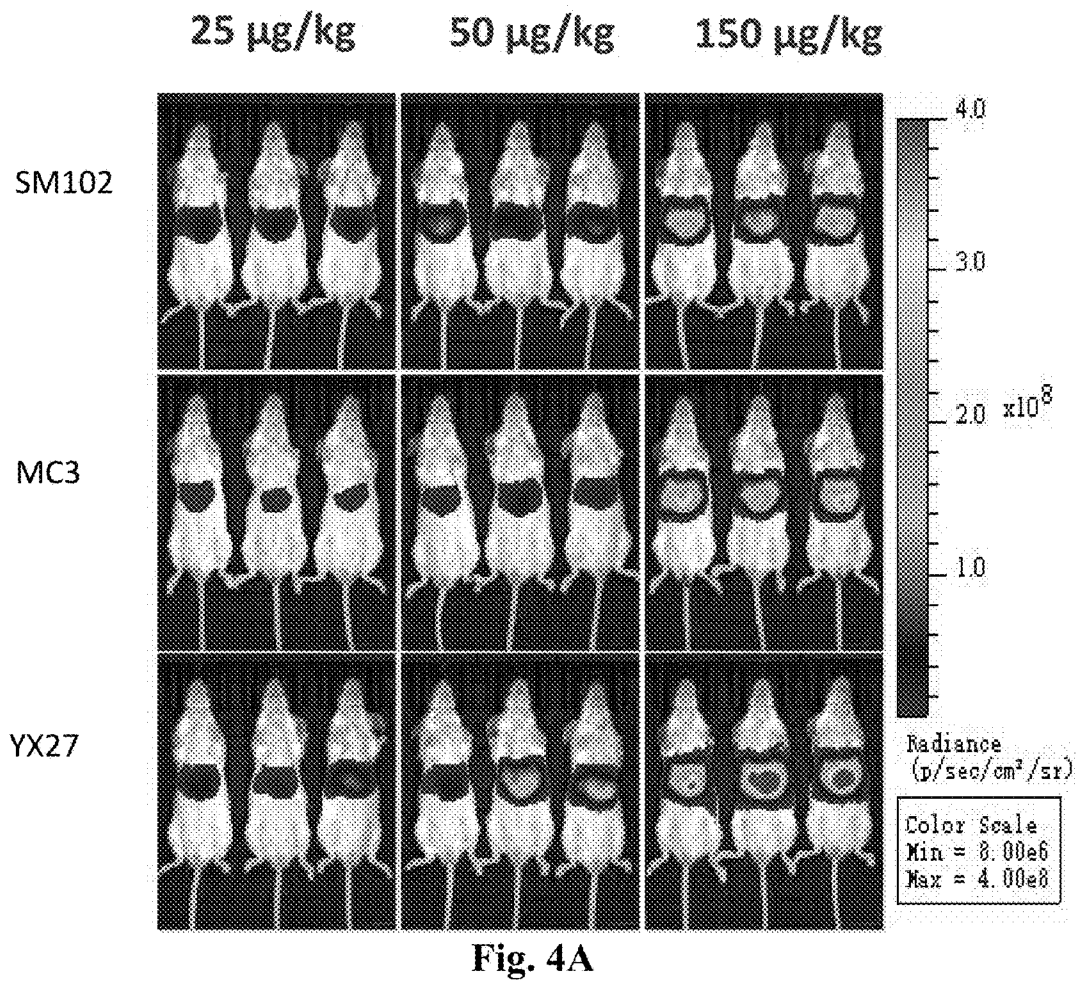
FIG. 4A shows whole-body bioluminescence imaging (in vivo imaging system, IVIS) 6 hours after delivery of YX27, SM102 and D-Lin-MC3-DMA (MC3) lipid nanoparticles, where mice were administered via tail vein (dose: 150 μg/kg).
Figure 4B:
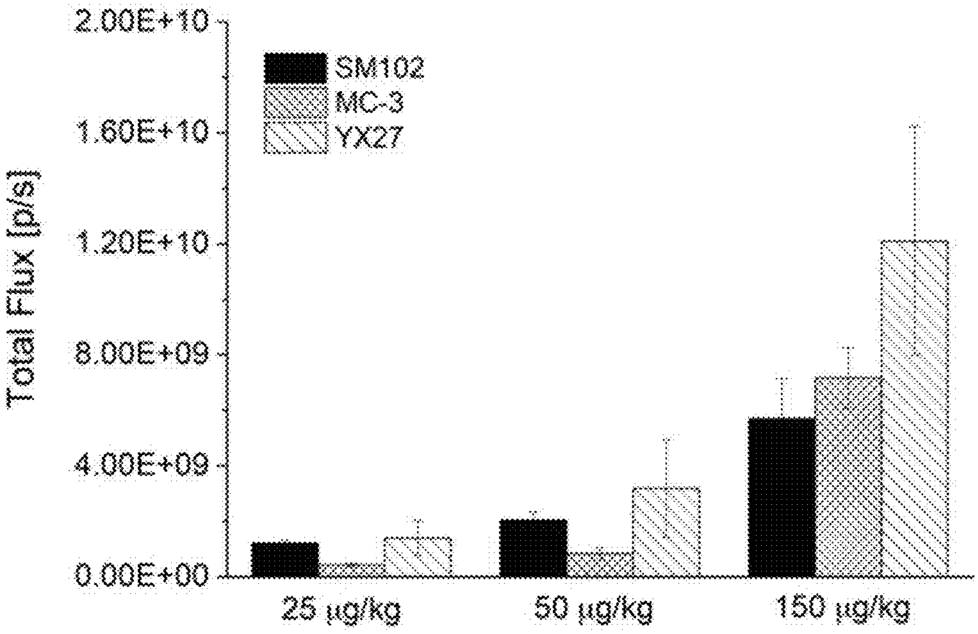
FIG. 4B shows the expression level of luciferase and bioluminescence intensity in liver tissue.

LNPs containing SM102 or MC3 as the cationic lipid and luciferase mRNAs at an N/P ratio of 7.5 were prepared according to the operation steps of Example 2, in which the dose of Fluc mRNAs was 25 μg/kg, 50 μg/kg or 150 μg/kg respectively; and then the mRNA delivery by the prepared LNPs and the expression and intensity of luciferase in the whole body, liver and other sites were studied by administration via tail vein. The delivery results are shown in FIG. 4A, FIG. 4B and the table below.

| Fluc mRNA dose | Average intensity | Standard deviation | Average intensity | Standard deviation | Average intensity | Standard deviation |
|---|---|---|---|---|---|---|
| | SM102 | | MC3 | | YX27 | |
| 25 μg/kg | 1.20E+09 | 1.02E+08 | 4.28E+08 | 6.06E+07 | 1.38E+09 | 6.27E+08 |
| 50 μg/kg | 2.02E+09 | 2.99E+08 | 8.40E+08 | 2.18E+08 | 3.16E+09 | 1.75E+09 |
| 150 μg/kg | 5.65E+09 | 1.45E+09 | 7.16E+09 | 1.09E+09 | 1.20E+10 | 4.12E+09 |

Unit: p/s

It can be seen from the above table that the ionizable lipid YX27 of the present invention exhibits superior delivery effect than the commercial cationic lipid SM102 or M at each mRNA dose.

Example 6: Time-Dependent Experiments of mRNA Delivery and Expression

Figure 5:
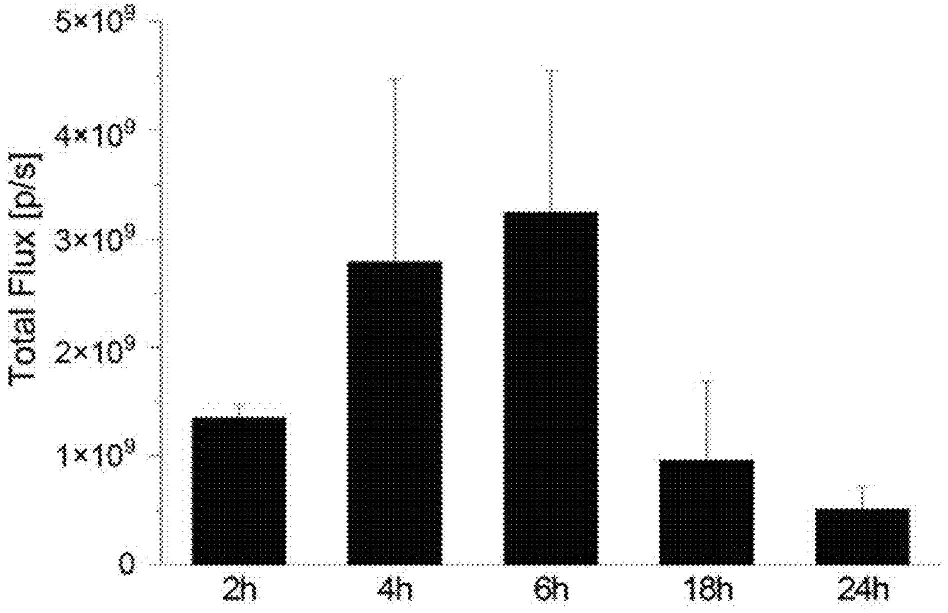
FIG. 5 shows a plot of the expression level of luciferase and bioluminescence intensity in liver tissue over time after delivery of firefly luciferase mRNAs by YX27 lipid nanoparticles.

In order to verify the expression efficiency of luciferase after administration of Fluc mRNA/LNPs as a function of time, YX27 solution encapsulating 150 μg/kg of Fluc mRNAs was injected into 6-8 week-old female Balb/c mice by administration via tail vein; 2 h, 4 h, 6 h, 18 h and 24 h after administration respectively, 200 μl of D-Lucifin (with a mass fraction of 30%) was injected by intraperitoneal administration, and the expression and intensity of luciferase in the whole body and liver site were detected by PerkinElmer IVIS Lumina III small animal in vivo optical imaging system. The delivery results are shown in FIG. 5 and the table below. It can be seen from the imaging results that the in vivo expression reached the peak at 6 h after the mRNA delivery.

| Time after administration | Average intensity | Standard deviation |
|---|---|---|
| 2 h | 1.47E+09 | 1.32E+08 |
| 4 h | 3.01E+09 | 1.72E+09 |
| 6 h | 3.51E+09 | 1.37E+09 |
| 18 h | 1.03E+09 | 7.34E+08 |
| 24 h | 5.49E+08 | 2.07E+08 |

Unit: p/s

Figure 6:
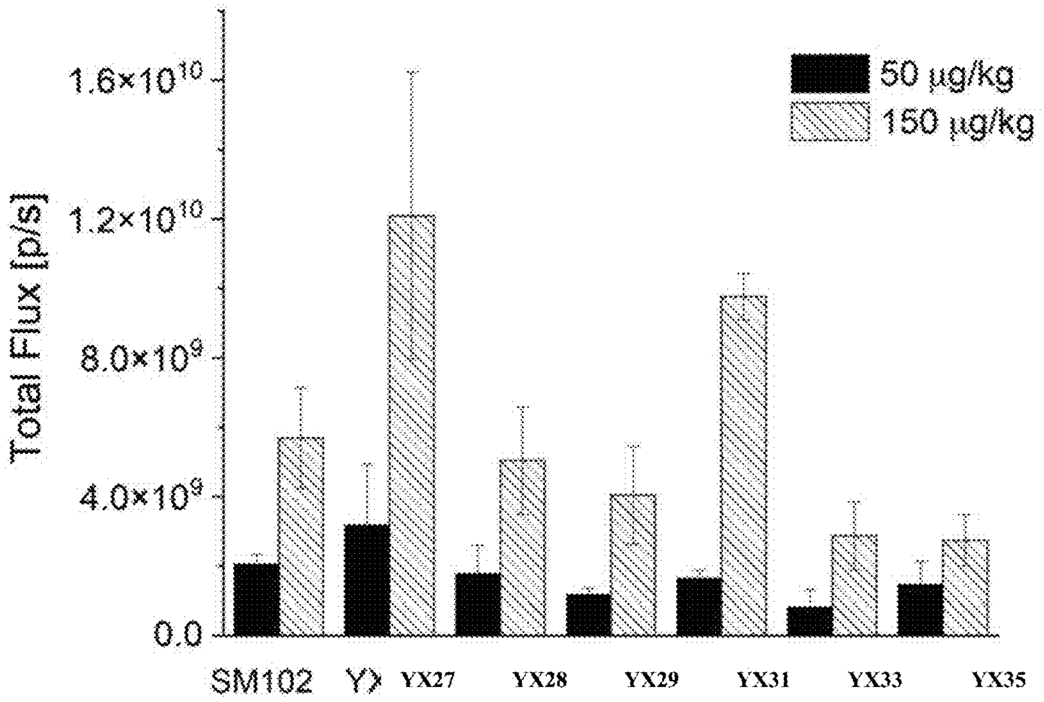
FIG. 6 shows the bioluminescence intensity of liver tissue 6 hours after delivery of firefly luciferase mRNAs by lipid nanoparticles with different molecular structures.

Example 7: Evaluation of mRNA Delivery Efficiency of YX Lipid Compounds with Different Structures LNPs containing SM102, YX27, YX28, YX29, YX33, YX31 or YX35 as the ionizable lipid compound and luciferase mRNAs at an N/P ratio of 7.5 were prepared according to the operation steps of Example 2, in which the dose of Fluc mRNAs was 150 μg/kg. The results of in vivo luciferase imaging luminescence intensity after delivery of Fluc mRNAs using different lipid compounds are shown in FIG. 6 and the table below. It can be found that when the number of carbon contained was 4 or 6, lipids having different amine heads can achieve efficient mRNA delivery, and the efficiency was close to that of commercial ionizable lipid SM102.

| Lipid No. | Average intensity | Standard deviation | Average intensity | Standard deviation |
|---|---|---|---|---|
| | 50 μg/kg | | 150 μg/kg | |
| SM102 | 2.02E+09 | 2.99E+08 | 5.65E+09 | 1.45E+09 |
| YX27 | 3.16E+09 | 1.75E+09 | 1.20E+10 | 4.12E+09 |
| YX28 | 1.88E+09 | 8.69E+08 | 5.29E+09 | 1.62E+09 |
| YX29 | 1.20E+09 | 2.06E+08 | 4.24E+09 | 1.39E+09 |
| YX33 | 8.19E+08 | 5.26E+08 | 2.97E+09 | 1.01E+09 |
| YX31 | 1.69E+09 | 2.42E+08 | 1.02E+10 | 6.64E+08 |
| YX35 | 1.50E+09 | 6.90E+08 | 2.83E+09 | 7.57E+08 |

Unit: p/s

The above description is only preferred embodiments of the present invention; however, the scope of protection of the present invention is not limited thereto. Any changes or substitutions readily conceivable to those familiar with the technical field within the technical scope disclosed by the present invention should be covered by the scope of protection of the present invention. Therefore, the scope of protection of the present invention should be based on the scope of protection of the claims.

The invention claimed is:

1. A lipid compound of formula (I), (I)

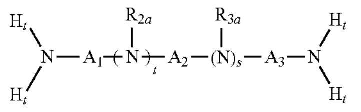

wherein $R_{2a}$ and $R_{3a}$ are each independently selected from the group consisting of hydrogen, a monovalent aliphatic group, a monovalent heteroaliphatic group, a monovalent aromatic group, a monovalent heteroaromatic group, and Ht;

t and s are each independently 0 or 1, and when t or s is zero, it means that the part is directly a single bond, provided that t and s are not both 0;

$A_1$, $A_2$, and $A_3$ are each independently selected from the group consisting of a single bond, a divalent aliphatic group, a divalent heteroaliphatic group, a divalent aromatic group, and a divalent heteroaromatic group;

each Ht is independently at each occurrence —$R_1$—X—$R_2$—Y—$R_3$—Z—$R_4$, wherein each $R_1$ is independently at each occurrence selected from the group consisting of a divalent aliphatic group, a divalent heteroaliphatic group, a divalent aromatic group, and a divalent heteroaromatic group;

each X is independently at each occurrence

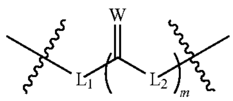, wherein m is 1-6;

W is selected from the group consisting of O, S, and $NR_c$;

$L_1$ is directly connected to $R_1$ and is selected from the group consisting of a single bond, O, S, and $NR_d$;

$L_2$ is selected from the group consisting of a bond, O, S, and $NR_e$;

wherein $R_c$, $R_d$, and $R_e$ are each independently selected from the group consisting of hydrogen, hydroxy, an oxyaliphatic group, a monovalent aliphatic group, a monovalent heteroaliphatic group, a monovalent aromatic group, and a monovalent heteroaromatic group;

Y and Z are both S;

each $R_2$ is independently at each occurrence selected from the group consisting of a single bond, a divalent aliphatic group, a divalent heteroaliphatic group, a divalent aromatic group, and a divalent heteroaromatic group;

$R_3$ is independently at each occurrence

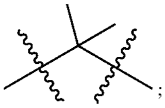 [SMILES: *C(*)(C)C];

each $R_4$ is independently at each occurrence a hydrophobic group selected from the group consisting of $-(CH_2CH_2O)_y-C_{3-8}$ alkyl, $-(CH_2CH_2O)_y-C_{3-8}$ alkenyl and $-(CH_2CH_2O)_y-C_{3-8}$ alkynyl, wherein y is 0 or 1 or 2.

2. The lipid compound of claim 1, wherein t is 0 and s is 1; or t is 1 and s is 0.

3. The lipid compound of claim 1, wherein $R_1$ is selected from the group consisting of a $C_{1-6}$ divalent aliphatic group and a $C_{1-6}$ divalent heteroaliphatic group.

4. The lipid compound of claim 1, wherein $L_1$ is selected from the group consisting of a single bond, O, S, and NH.

5. The lipid compound of claim 1, wherein X is

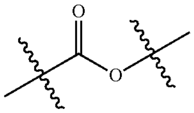, 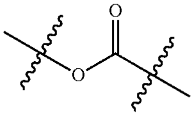,

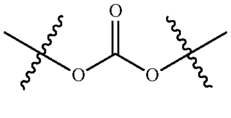, 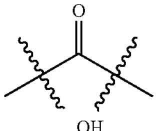,

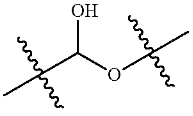, 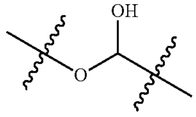,

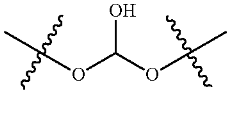, 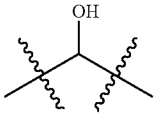,

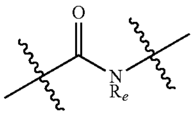, 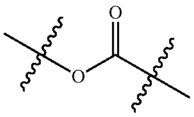,

-continued

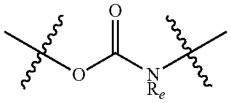, 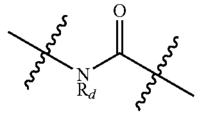,

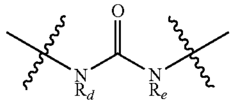 or 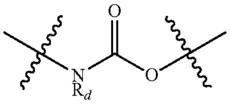, wherein $R_d$ and $R_e$ are as defined for formula (I) in claim 1.

6. The lipid compound of claim 5, wherein $R^d$ and $R^e$ are each independently selected from the group consisting of H and a $C_{1-4}$ monovalent aliphatic group.

7. The lipid compound of claim 1, wherein each $R_2$ is independently at each occurrence selected from the group consisting of a single bond and a $C_{1-6}$ divalent aliphatic group.

8. The lipid compound of claim 7, wherein each $R_2$ is independently at each occurrence $C_{1-4}$ divalent aliphatic group.

9. The lipid compound of claim 1, wherein each $R_4$ is independently at each occurrence selected from the group consisting of $C_{3-8}$ alkyl, $C_{3-8}$ alkenyl, $C_{3-8}$ alkynyl, $(CH_2CH_2O)-C_{3-8}$ alkyl, $(CH_2CH_2O)-C_{3-8}$ alkenyl, $(CH_2CH_2O)-C_{3-8}$ alkynyl, $(CH_2CH_2O)_2-C_{3-8}$ alkyl, $(CH_2CH_2O)_2-C_{3-8}$ alkenyl and $(CH_2CH_2O)_2-C_{3-8}$ alkynyl; or each $R_4$ is independently at each occurrence selected from the group consisting of $C_{4-8}$ alkyl, $C_{4-8}$ alkenyl, $C_{4-8}$ alkynyl, $(CH_2CH_2O)-C_{4-8}$ alkyl, $(CH_2CH_2O)-C_{4-8}$ alkenyl, $(CH_2CH_2O)_2-C_{4-8}$ alkynyl, $(CH_2CH_2O)_2-C_{4-8}$ alkyl, $(CH_2CH_2O)_2-C_{4-8}$ alkenyl and $(CH_2CH_2O)_2-C_{4-8}$ alkynyl.

10. The lipid compound of claim 9, wherein the alkyl in the $C_{4-8}$ alkyl, $(CH_2CH_2O)-C_{4-8}$ alkyl or $(CH_2CH_2O)_2-C_{4-8}$ alkyl is a linear alkyl; the alkenyl in the $C_{4-8}$ alkenyl, $(CH_2CH_2O)-C_{4-8}$ alkenyl or $(CH_2CH_2O)_2-C_{4-8}$ alkenyl is a linear alkenyl; and the alkynyl in the C4-8 alkynyl, $(CH_2CH_2O)-C_{4-8}$ alkynyl or $(CH_2CH_2O)_2-C_{4-8}$ alkynyl is a linear alkynyl.

11. The lipid compound of claim 9, wherein each $R_4$ is independently at each occurrence selected from the group consisting of $-(CH_2CH_2O)-(CH_2)_3CH_3$, $-(CH_2CH_2O)_2-(CH_2)_3CH_3$, $-(CH_2CH_2O)-(CH_2)_4CH_3$, $-(CH_2CH_2O)_2-(CH_2)_4CH_3$, $-(CH_2CH_2O)-(CH_2)_5CH_3$, $-(CH_2CH_2O)_2-(CH_2)_5CH_3$, $-(CH_2CH_2O)-(CH_2)_6CH_3$, $-(CH_2CH_2O)_2-(CH_2)_6CH_3$, $-(CH_2CH_2O)-(CH_2)_7CH_3$ and $-(CH_2CH_2O)_2-(CH_2)_7CH_3$.

12. The lipid compound of claim 1, wherein each Ht is independently at each occurrence

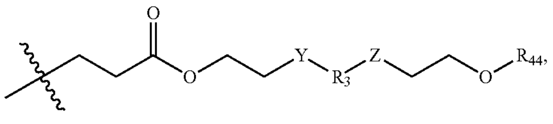, wherein Y and Z are both S; or Y is S and Z is O; or Y is O and Z is S; or Y and Z are both O; each $R_3$ is independently at each occurrence

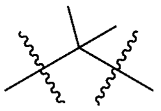 [SMILES: *C(*)(C)C]

and $R_{44}$ is $C_{4-8}$ alkyl, $C_{4-8}$ alkenyl or $C_{4-8}$ alkynyl.

13. The lipid compound of claim 12, wherein each $R_{44}$ is independently at each occurrence selected from the group consisting of $-(CH_2)_3CH_3$, $-(CH_2)_4CH_3$, $-(CH_2)_5CH_3$, $-(CH_2)_6CH_3$ and $-(CH_2)_7CH_3$.

14. The lipid compound of claim 1, wherein t is 1, s is 0, $A_2$ is a single bond, and $A_1$ and $A_3$ are each independently selected from the group consisting of a divalent aliphatic group and a divalent heteroaliphatic group; or t is 1, s is 0, $A_2$ is a single bond, and $A_1$ and $A_3$ are each independently a $C_{1-6}$ divalent aliphatic group; or t is 1, s is 0, $A_2$ is a single bond, $A_1$ and $A_3$ are each independently selected from the group consisting of $-CH_2CH_2-$ and $-CH_2CH_2CH_2-$, and $R_{2a}$ is selected from the group consisting of hydrogen and a monovalent aliphatic group.

15. The lipid compound of claim 1, wherein t is 1, s is 1, and $A_1$, $A_2$ and $A_3$ are each independently selected from the group consisting of a divalent aliphatic group and a divalent heteroaliphatic group; or t is 1, s is 1, and $A_1$, $A_2$ and $A_3$ are each independently a $C_{1-6}$ divalent aliphatic group; or t is 1, s is 1, and $A_1$, $A_2$ and $A_3$ are each independently selected from the group consisting of $-CH_2CH_2-$ and $-CH_2CH_2CH_2-$, and $R_{2a}$ and $R_{3a}$ are each independently selected from the group consisting of hydrogen and a monovalent aliphatic group.

16. The lipid compound of claim 1, wherein

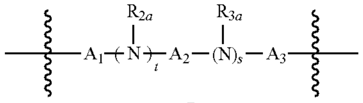

is

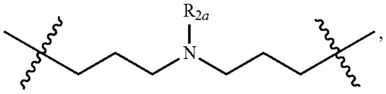

,

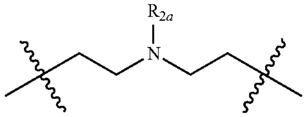

or

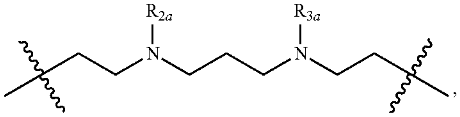

, wherein $R_{2a}$ and $R_{3a}$ are each independently selected from the group consisting of hydrogen and a monovalent aliphatic group.

17. A lipid compound selected from the group consisting of

YX17

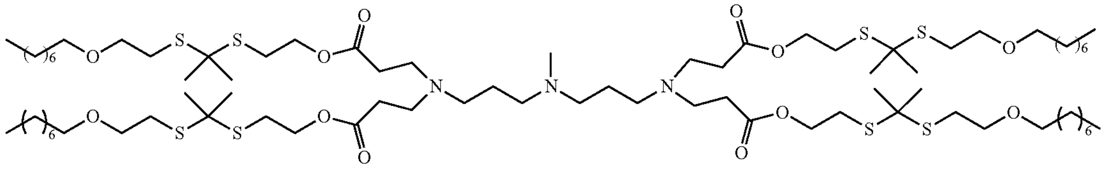

YX31

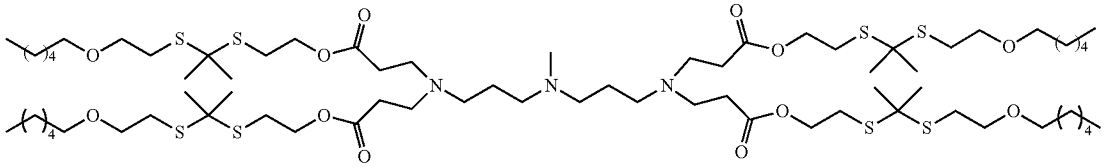

YX27

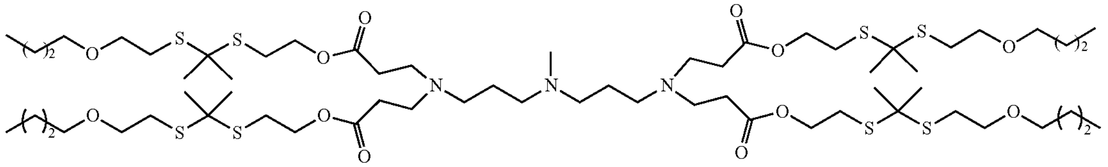

YX28

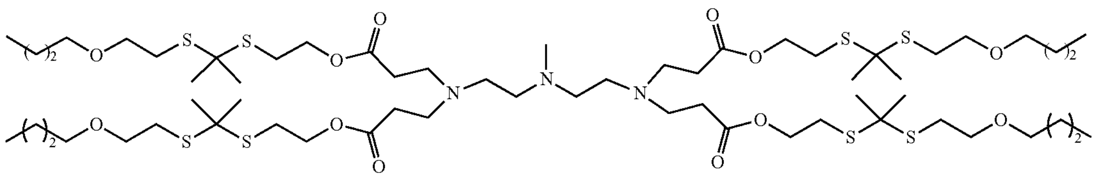

-continued

YX35

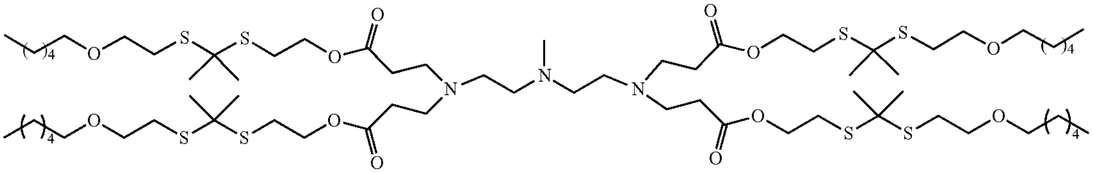

YX29

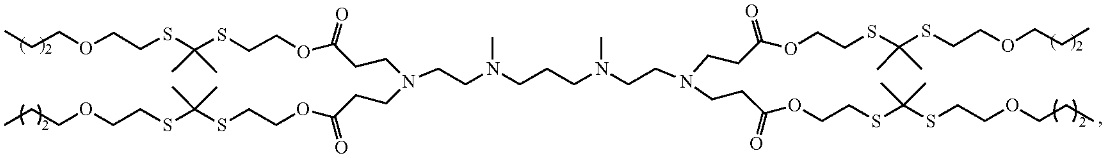

and

YX33

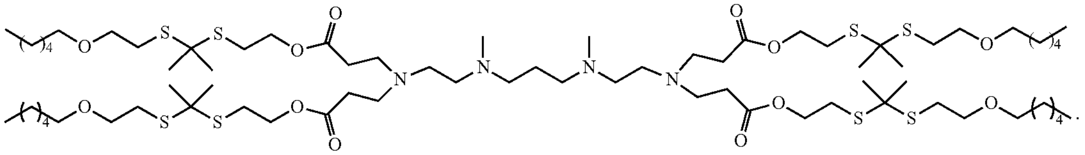

18. A pharmaceutical composition comprising a pharmaceutical carrier and a lipid nanoparticle, wherein the lipid nanoparticle comprises the lipid compound of claim 1 and a pharmaceutically active molecule.

19. A method for regulating gene expression comprising delivering a nucleic acid to a cell, the method comprising: contacting the cell with the pharmaceutical composition of claim 18 under conditions sufficient to cause uptake of the nucleic acid into the cell.

* * * * *